US008795175B2

(12) United States Patent
Funane et al.

(10) Patent No.: US 8,795,175 B2
(45) Date of Patent: Aug. 5, 2014

(54) BIOLOGICAL MEASUREMENT SYSTEM MEASURING CEREBRAL BLOOD VOLUME CHANGES TO FIND DISEASE OR DANGER

(75) Inventors: Tsukasa Funane, Hatoyama (JP); Naoki Tanaka, Tokyo (JP); Hideaki Koizumi, Tokyo (JP); Atsushi Maki, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 1387 days.

(21) Appl. No.: 12/252,809

(22) Filed: Oct. 16, 2008

(65) Prior Publication Data

US 2009/0143654 A1    Jun. 4, 2009

(30) Foreign Application Priority Data

Oct. 18, 2007    (JP) ................. 2007-270819

(51) Int. Cl.
*A61B 5/00* (2006.01)
*A61B 5/02* (2006.01)

(52) U.S. Cl.
USPC ............................ 600/309; 600/481; 600/485

(58) Field of Classification Search
None
See application file for complete search history.

(56) References Cited

U.S. PATENT DOCUMENTS

| 2004/0082862 | A1* | 4/2004 | Chance | 600/473 |
|---|---|---|---|---|
| 2005/0131284 | A1* | 6/2005 | Grinvald et al. | 600/323 |
| 2005/0192490 | A1* | 9/2005 | Yamamoto et al. | 600/310 |
| 2006/0122523 | A1* | 6/2006 | Bonmassar et al. | 600/506 |
| 2007/0213619 | A1* | 9/2007 | Linder | 600/481 |
| 2007/0287922 | A1* | 12/2007 | Tanaka et al. | 600/485 |

FOREIGN PATENT DOCUMENTS

JP          9-091408          4/1997

OTHER PUBLICATIONS

Maki, et al, Medical Physics, Dec. 1995, vol. 22, No. 12, pp. 1997-2005.
Schroeter, et al, Journal of Cerebral Blood Flow & Metabolism, pp. 1183-1191, 2004.
Schroeter, et al, Journal of Cerebral Blood Flow & Metabolism, pp. 1675-1684, 2005.
Castiglioni, et al, IEEE, pp. 465-466, 1992.
Themelis, et al, Journal of Biomedical Optics, Jan./Feb. 2007.
Y. Ichimaru, et al., BME, vol. 8, No. 10, 1994, pp. 36-48.
Rasmussen, P., et al. Journal of Cerebral Blood Flow & Metabolism (2007) 27, 1082-1093.

* cited by examiner

*Primary Examiner* — Shanon A Foley
(74) *Attorney, Agent, or Firm* — Brundidge & Stanger, P.C.

(57) ABSTRACT

Cerebral blood volume changes are measured to evaluate, from properties of low-frequency components of such changes and heart rate changes calculated by analysis, a distribution of cerebral blood vessel hardness and its change over time to thereby estimate and display diseased and dangerous portions based on the evaluation. This is attainable by a biological measurement system having a cerebral blood volume measurement unit which measures a regional cerebral blood volume of a body under test, an analyzer unit that analyzes a signal measured by the cerebral blood volume measurement unit, an extraction unit for extracting, based on an output of the analysis unit, information concerning a regional cerebral blood vessel state of the test body, and a display unit which displays a measurement result of the cerebral blood volume measurement unit, an analysis result of the analyzer unit or an extraction result of the extraction unit.

17 Claims, 24 Drawing Sheets

SYSTEM CONFIGURATION DIAGRAM

FIG.2

INFORMATION INPUT SCREEN

CEREBRAL VASCULAR DISTURBANCE TEST

DATE OF TEST ☐ ☐ ☐
      MONTH DAY  YEAR
PATIENT NO.
DIAGNOSIS INFO ☐
1. DEFINITIVE DIAGNOSIS? : YES ☐   NO ☐
2. DIAGNOSIS DATA

MEASUREMENT PROBE

POWER SPECTRUM LOW-FREQUENCY COMPONENT (CBV)

EXAMPLE OF 2D MAPPING RESULT OF Rp-BASED ARTERIAL SCLEROSIS DIAGNOSIS RESULTS AT HEAD

EXAMPLE OF LEAST-SQUARE FITTING TO 1/f$^\alpha$ LINE IN CBV POWER SPECTRUM DOUBLE-LOGARITHMIC GRAPH POWER SPECTRUM OF CBV, pCBV DISPLAY OF CALCULATION RESULT OF AVERAGE VALUE OF MAPPED Rp (Systemic) OF RESPECTIVE MEASUREMENT PORTIONS AND DECISION RESULT OF ARTERIAL SCLEROSIS DEGREE FLOW OF AGING/ILLNESS JUDGMENT BASED ON $\alpha$ OF $1/f^{\alpha}$ DISPLAY EXAMPLE OF DECISION RESULT OF AGE / ILLNESS FROM 1/f FLUCTUATION POWER SPECTRUM OF pCBV, HEART RATE SYSTEM CONFIGURATION FOR SIMULTANEOUS MEASUREMENT OF REGIONAL BLOOD VOLUME CHANGES AT BRAIN AND HEART OR MYELON MEASUREMENT DATA OF OXYGENATED HEMOGLOBIN CONCENTRATION CHANGE UPON SIMULTANEOUS MEASUREMENT, USING REGIONAL BLOOD VOLUME CHANGE MEASUREMENT UNITS, OF FIVE PORTIONS BY PROBES PLACED AT A LOCATION ON THE HEAD, A LOCATION IMMEDIATELY OVERLYING THE HEART, A LOCATION ABOVE THE SPINE (WAIST POSITION) AND LOCATIONS JUST ABOVE RADIAL ARTERY (RIGHT AND LEFT HANDS)

DISPLAY EXAMPLE OF A PHASE DIFFERENCE DISTRIBUTION OF INTRABRAIN PULSE WAVE AND SPECIFIC-REGION PULSE WAVE ALONG WITH A DIAGNOSIS RESULT

DISPLAY EXAMPLE OF CEREBRAL BLOOD FLOW DISTRIBUTION ESTIMATED
FROM INTRABRAIN PULSE WAVE SHAPE

FIG.24

MATHEMATICAL EXPRESSIONS IN DESCRIPTION

EQUATION 1
$$R_p(CBV) = P_{LF}(CBV)/P_{VLF}(CBV)$$

EQUATION 2
$$\log P(f) = -\alpha \log f + \beta$$

EQUATION 3
$$R_p(Systemic) = P_{LF}(pCBV)/P_{VLF}(pCBV)$$

FORMULA 4
$$R_p(Systemic) < TH1$$

FORMULA 5
$$R_p(CBV) < TH1$$

FORMULA 6
$$R_p(CBV)/R_p(Systemic) < TH2$$

BIOLOGICAL MEASUREMENT SYSTEM MEASURING CEREBRAL BLOOD VOLUME CHANGES TO FIND DISEASE OR DANGER

INCORPORATION BY REFERENCE

The present application claims priority from Japanese application JP 2007-270819, filed on Oct. 18, 2007, the content of which is hereby incorporated by reference into this application.

BACKGROUND OF THE INVENTION

This invention relates to biological measurement systems for performing noninvasive inspection of cerebral vasculopathy.

The cerebral vasculopathy (or apoplexy) is a generic term of those diseases which bring nervous symptoms due to organic or functional abnormalities of cerebral blood vessels, and presently it is ranked at the third place of causes of death of Japanese people. About seventy percent of cerebral vascular disturbances is the necrosis (softening or "malacia") of brain organization occurring due to arterial sclerosis, i.e., ischemia, and involves cerebral thrombosis due to atheromatous hardening of artery in the brain and cerebral embolism due to embolization from outside of the cranium or brainpan. Examples of bleeding include cerebral apoplexy with effusion of blood to inside of brain parenchyma and subarachnoid hemorrhage with bleeding into subarachnoid cavity. Inspection in the acute stage is performed by blood examination, electrocardiogram and X-ray computed tomography (CT), etc. Magnetic resonance imaging (MRI), positron emission tomography (PET), single-photon emission computed tomography (SPECT) or cerebral blood vessel photography is employable as auxiliary inspection therefor.

Regional blood volume changes in a brain are noninvasively measurable by optical topography methodology. The optical topography is a method having the steps of irradiating light onto a body being tested, which light has its wavelength belonging to the visible to infrared range, and detecting by the same photodetector a plurality of light rays of those signals that have passed through inside of the test body to thereby measure a hemoglobin change amount (as disclosed in JP-A-9-019408 or else). Its feature lies in that the restrictiveness against the person under test is kept low when compared to brain function measurement techniques, such as MRI, PET, etc.

However, the cerebral vascular disturbance inspection stated above have a risk of using invasive methods and a penalty of forcing persons under testing in some cases to bear the burden even when a method used is not the invasive one. In addition, it was higher in possibility of overlooking small nidi. Accordingly, it has been difficult to perform the cerebral vascular disturbance examination in a preventive manner. Additionally, with commercially available supersonic wave-based blood vessel hardness inspection apparatus, the brain per se is not observed so that it was impossible to directly estimate arterial sclerosis by direct measurement of the brain. Regarding a phase difference of pulse waves of a plurality of portions also, in the case where a plurality of types of inspection tools are used, system-dependent time delays can occur, thereby making it difficult to measure such phase difference with a required level of accuracy.

SUMMARY OF THE INVENTION

Accordingly, this invention measures cerebral blood volume changes to evaluate, from the nature of low frequency components of such changes and heart rate variations to be calculated by analysis, cerebral blood vessel hardness and its change with time to thereby estimate and display a diseased portion(s) and a dangerous part(s) based on the evaluation. In addition, one part of the same system that measures cerebral blood volume variations is used for the measurement of extracerebral portions to thereby perform simultaneous measurement.

According to this invention, it becomes possible to noninvasively inspect cerebral vascular disturbance with a high degree of accuracy.

Other objects, features and advantages of the invention will become apparent from the following description of the embodiments of the invention taken in conjunction with the accompanying drawings.

BRIEF DESCRIPTION OF THE DRAWINGS

FIG. 2 is an information input display screen of the biological measurement system.

FIG. 24 shows equations used in the description.

DESCRIPTION OF THE INVENTION

Embodiments of this invention will be explained with reference to the accompanying drawings below.

Embodiment 1

Figure 1:
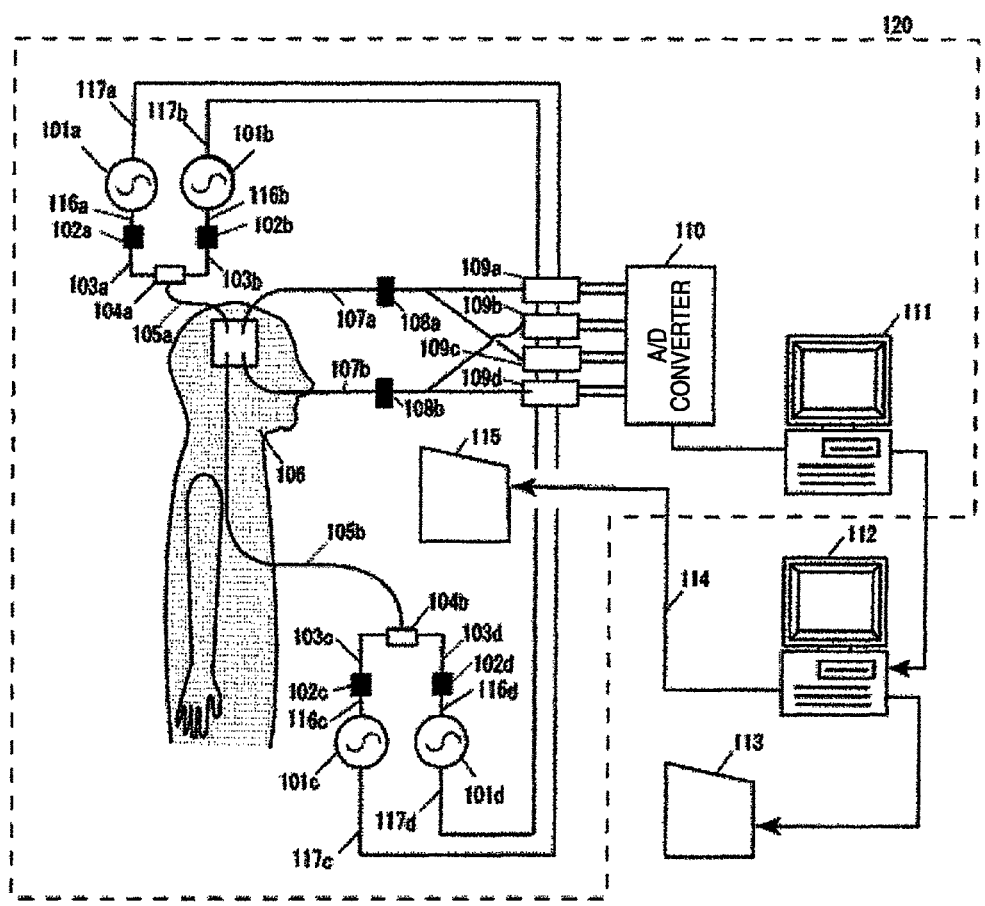
FIG. 1 is a diagram showing an arrangement of a biological measurement system embodying the invention.

A configuration of apparatus is shown in FIG. 1. This apparatus is generally made up of an input unit, analysis unit, storage unit and extraction unit, which are included in a computer 112, and further includes a cerebral blood volume measurement unit 120 and a display unit 113. Note that in case the computer 112 has a display function, the display unit 113 is replaceable thereby.

At the input unit, information necessary for inspection is input by an operator, including the age of a person being tested, sexuality, dominant hand, diagnosis at a present time, and diagnosis data such as medical treatment history—in particular, whether definitive diagnosis result is available or not. An exemplary data input display screen to be presented in such case is shown in FIG. 2. Although in this example a patient number is used for identification, his or her name may be used alternatively. In a case where the definitive diagnosis result is available, a blank square box of item #1 is checked. In such case, the inspection result is stored in a database in an automated way.

A local or regional brain blood volume (oxygenated hemoglobin, deoxygenated hemoglobin, total hemoglobin) was obtained in a way which follows: in the cerebral blood volume measurement unit 120, light with its wavelength belonging to a range of from the visible light to infrared ray is irradiated onto the head of a body being tested, i.e., subject; then, light rays of a plurality of signals that have passed through inside of the subject are detected and measured by the same photodetector. Within a time period of the measurement, appropriate excitement and order were given to the subject by an excitement/order induction device 115. The excitement/order induction device 115 is controlled by a control signal 114 which is sent from the computer 112.

There are provided a plurality of light sources 102a to 102d which are different in wavelength from one another (if two kinds of wavelengths are used, an example is that the light source 102a and 102c are set at 695 nm whereas the light sources 102b and 102d are at 830 nm), modulators or oscillators 101a and 101b (101c and 101d) for intensity modulation of light rays of the plurality of light sources 102a and 102b (102c and 102d) at mutually different frequencies by way of drive signal lines 116a and 116b (116c and 116d), a plurality of light irradiation means for irradiating the light from a coupler 104a (104b)—this is for coupling together the intensity-modulated light rays through optical fibers 103a and 103b (103c and 103d) respectively—onto a head skin of a person 106 being tested, which is a subject, through a light irradiation-use optic fiber 105a (105b), and a plurality of light-receiving means comprised of photo-detectors 108a and 108b, which are provided at respective ones of light-receiving optic fibers 107a and 107b in such a manner that their leading edges are placed at a position in close proximity to a light irradiation position of the plurality of light irradiation means with a preset distance (here, set at 30 mm) from the light irradiation position. At the light-receiving optic fiber 107a, 107b, the living-body pass-through light is collected at the optic fiber, followed by photoelectric conversion of the live-body pass-through light at the respective photodetector 108a, 108b, respectively. The light-receiving means is the one that detects light reflected from inside of the test body and converts it into an electrical signal, wherein photoelectric conversion elements are used as the photodetectors 108, representative examples of which are photoelectron multiplier tubes and photodiodes. Although in FIG. 1 an explanation is given of one case where two kinds of wavelengths are used, it is also possible to use more than three kinds of wavelengths. Additionally, it is also possible to perform similar measurement while disposing a plurality of light irradiation means and a plurality of light-receiving means, respectively.

Electrical signals indicative of live-body pass-through light intensities as photoelectrically converted by the photodetectors 108a, 108b (to be referred to as live-body penetration light intensity signals) are input to lock-in amplifiers 109a-109d, respectively. Also input to the lock-in amps 109a-109d are reference signals 117a-117d from the oscillators (modulators) 101a and 101b (101c and 101d). For example, at 109a or 109b, light rays with the wavelength of 695 nm of the light sources 102a and 102c are output in a split manner, which will be taken out through lock-in processing; at 109c, 109d, 830-nm wavelength light rays of the light sources 102b and 102d are split and output. At this time, it is assumed that measurement points are two points, one of which is between a light-sending probe 201a and a light-receiving probe 202a, and the other of which is between a light-sending probe 201b and light-receiving probe 202b.

The separated penetration light intensity signal of respective wavelengths as output from the lock-in amplifiers 109a-109d are each subjected to analog-to-digital conversion at an analog-to-digital converter (to be referred to hereinafter as A/D converter) 110 and then sent forth toward a measurement control computer 111. At this measurement control computer 111, the penetration light intensity signals are used to compute, from a detection signal of each detection point, relative change amounts of oxygenated hemoglobin concentration, deoxygenated hemoglobin concentration and total hemoglobin concentration in accordance with the procedure as has been described in the A. Maki et al., Medical Physics, Vol. 22, pp. 1997-2005 (1995), which amounts are then stored in the storage device as change-with-time information of a plurality of measured points.

It should be noted that although the example was stated here which is for performing A/D conversion after having performed the lock-in processing, it is also possible to digitally perform the lock-in processing after completion of amplification and A/D conversion of signals from the photodetectors.

Also note that the embodiment was stated here which performs the splitting of a plurality of light rays by modulation methodology, this is not a limitative one; for example, it is also possible to use time-division techniques for separating a plurality of light rays by shifting along the time axis the timing of irradiating two or more light rays.

At the analysis unit, it performs analysis of power spectrum of the above-noted regional brain blood volume thus measured although details will be described later. These results are passed to the storage unit within the computer 112.

At the storage unit, it temporarily stores measurement information of the person under inspection and enables execution of later processing; on the other hand, it is also possible to store the measurement information as a database in case the definitive diagnosis is available, for example.

At the extraction unit within the computer 112, it extracts information as to blood vessel disturbance, by a method as will be described later, from the power spectrum of the signal that has been analyzed by the above-noted analysis unit and the quantitative information relating thereto. The blood vessel disturbance-relating information that was extracted at the above-noted extraction unit is displayed at the display unit 113.

It is noted here that although in FIG. 1 the computer 111 and the computer 112 are depicted separately, it is needless to say that these may be combined together into a single computer.

Figure 3:
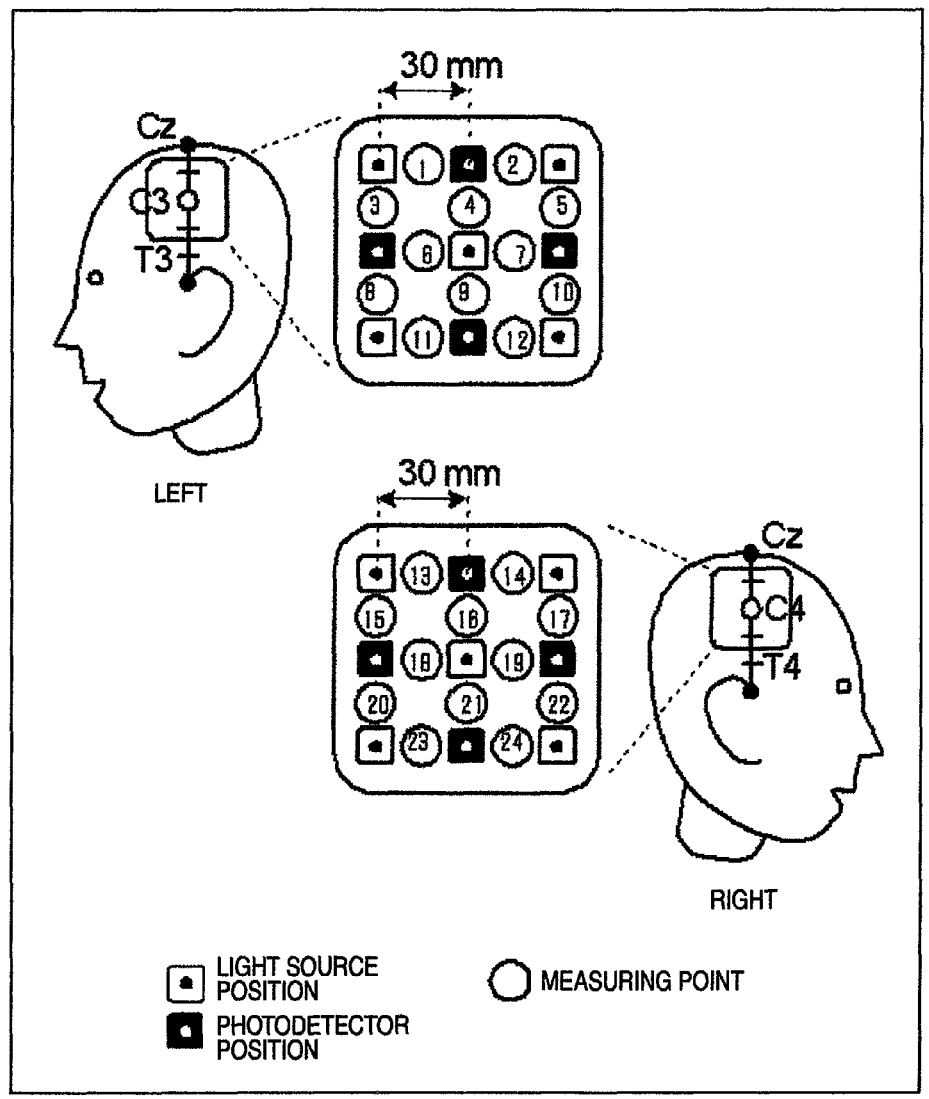
FIG. 3 shows an example of measurement probe layout.

FIG. 3 pictorially explains the probes for measurement of the cerebral blood volume. Cz, T3 and T4 are symbols (international 10-20 method) indicating standard positions for brain wave measurement, which represent the top of a head, a portion immediately above the left ear, and a portion just above the right ear, respectively. C3 and C4 are intermediate points of Cz and T3 and Cz and T4, respectively. Twelve (12) channels are provided for each of the right and left sides, thereby enabling measurement of 24 channels in total. Each channel is identified by a number which is added to a measurement point (referred to as the channel number hereinafter).

Figure 4:
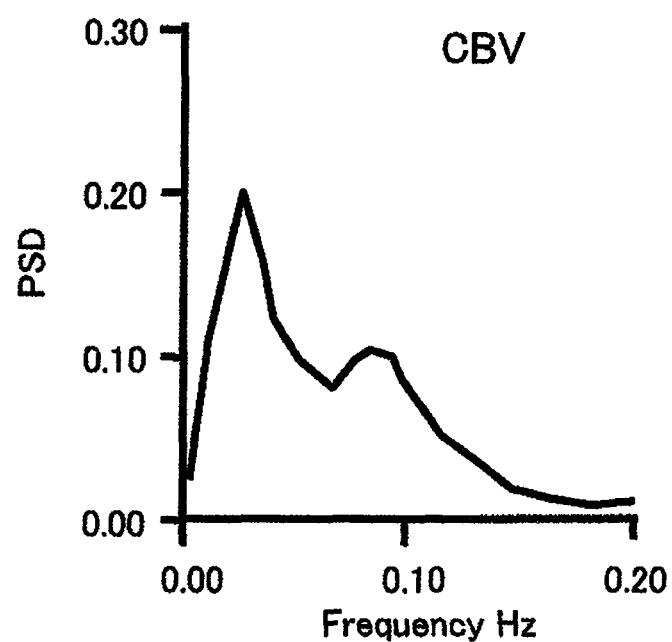
FIG. 4 shows a power spectrum low-frequency component of regional cerebral blood volume (CBV).

An example of the power spectrum that was obtained at the above-noted analyzer unit is shown in FIG. 4. It is the power spectrum of a regional cerebral blood volume (CBV). The vertical axis represents power spectrum density (PSD). The power spectrum density is the one that is normalized in such a way as to become 1 when the power is integrated about the frequency. The frequency of the abscissa axis includes a range of from zero Hz up to Nyquist frequency (the half of a sampling frequency) in a coordinate system which corresponds to the time axis that is obtainable by Fourier transformation of variations in blood pressure and heart rate, which are time-sequence data. In FIG. 4, a portion of it is shown.

$P_{LF}$ The result shown in FIG. 4 is calculated from a regional brain blood volume variation which was measured at a channel of FIG. 3, as an example. Two peaks exist on the spectrum, and a ratio $R_P=P_{LF}/P_{VLF}$ is calculated, where $P_{LF}$ is the average power of low-frequency (LF) region (0.06 to 0.11 Hz), and $P_{VLP}$ is the average power of very-low-frequency (VLF) domain (0.01-0.05 Hz). The power ratio $R_P$ is calculated based on the average power value in each region in the way stated supra. Alternatively, it may be computed from the ratio of power integration values in corresponding frequency domains. This computation may be done by use of the power after having removed system noises therefrom by an appropriate method.

$R_P$ Fluctuation of these frequency domains is deeply related to the adjustment functionality of blood vessel system. While the adjustment is controlled by vasomotor nerve center, sympathetic nerve, parasympathetic nerve (pneumogastric nerve), etc., the origin of the fluctuation includes neurogenic and myogenic portions. In the Journal of Cerebral Blood Flow & Metabolism, Vol. 24, pp. 1183-1191 (2004) and the Journal of Cerebral Blood Flow & Metabolism, Vol. 25, pp. 1675-1684 (2005) by M. L. Schroeter et al., there are described the facts which follow: aging leads to a decrease in LF region component of cerebral blood volume variation, with no significant changes being recognized for VLF region component; and, microvascular disease or "microangiosis" results in a decrease in each of the LF region component and VLF region component of cerebral blood volume variation, with the decrease in LF region component being more severe than that of the other. The aging-caused change is deeply related to the textile-conversion phenomenon of smooth muscle whereas the microangiosis-caused change is deeply related to blocking/hardening phenomena of fine/narrow blood vessels due to the presence of a thrombus. Any one of these changes is thought to be caused by denaturalization of smooth muscle tissues. The above-noted power ratio tends to become smaller in value due to the aging and also due to the microangiosis. More precisely, it can be said that the fluctuation of LF region is more myogenic when compared to the fluctuation of VLF region.

$R_P$ As the power ratio obtained in this way becomes smaller, the blood vessel at such portion is judged to be harder. For example, as in FIG. 5, it becomes possible to indicate which portion of the head is relatively greater in hardness of blood vessel, by performing two-dimensional (2D) mapping of the state of head blood vessel(s) to be judged from $R_P$.

Figure 6:
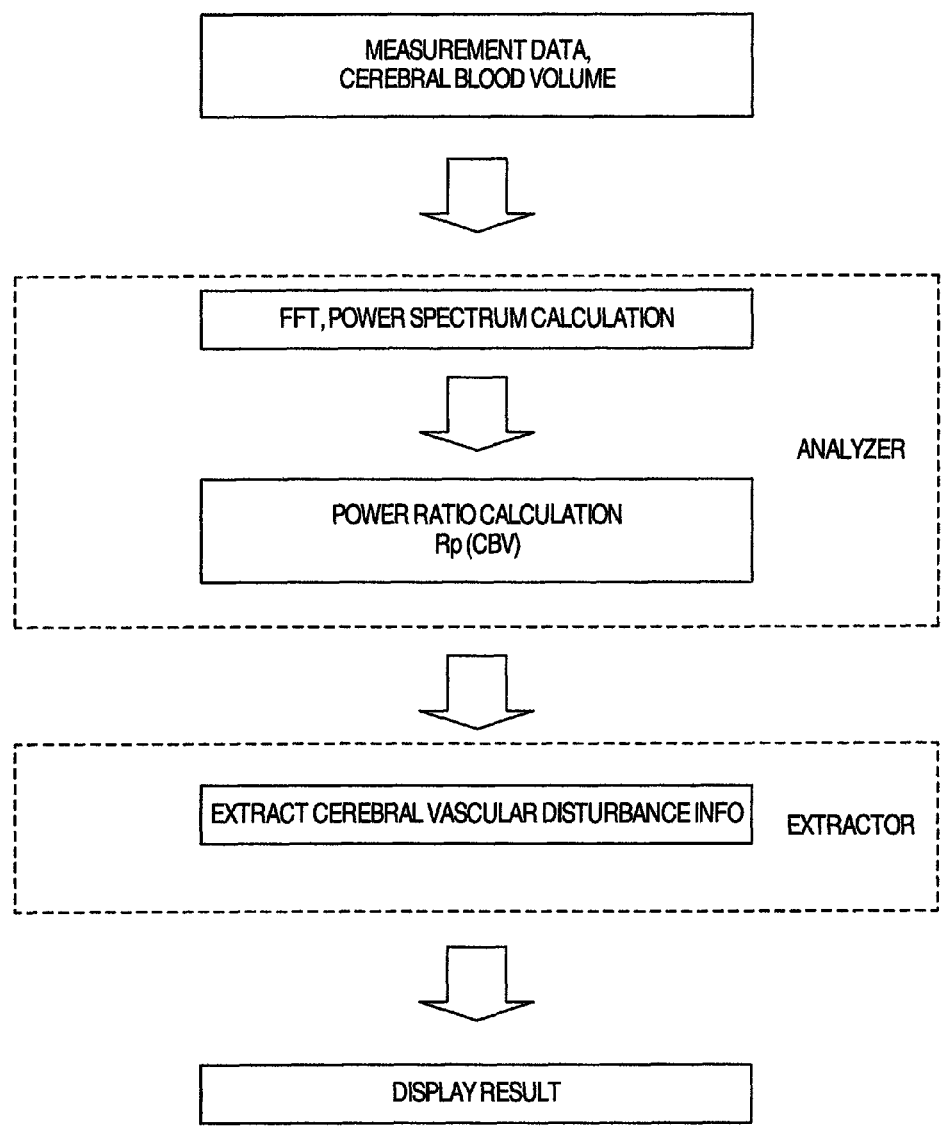
FIG. 6 shows a flow of a procedure for assistance of diagnosis of cerebral blood disturbance, such as arterial sclerosis by means of $R_P$.

Additionally, $R_P$ that is directly obtainable from the power spectrum of cerebral blood volume variation is noted as $R_P$ (CBV). In short, $R_P$ (CBV) is represented as [Equation 1] in FIG. 24. This makes it possible to use it for judgment of an arterial sclerosis portion(s). A summarized flow of the processing of from acquisition of measurement data up to display of a result—especially, at the analyzer unit and extraction unit—is shown in FIG. 6. From cerebral blood volume data, the power spectrum is calculated by fast Fourier transform (FFT). While power spectrum calculation methodology includes various methods, such as a nonparametric method, e.g., Welch method, and parametric method, e.g., Yule method, any one of them is employable. Next, from the power spectrum thus obtained, the power ratio $R_P$ (CBV) is calculated by the above-stated method. At the extraction unit, the information as to cerebral vascular disturbance is extracted based on the resulting power ratio; at the display unit, such result is displayed.

Further note here that in the power spectrum of regional cerebral blood volume that was obtained by the procedure of the embodiment 1, it is also possible to extract a heart-beat fundamental wave component and exclude therefrom system noise portions when the need arises and, thereafter, display a full-width-at-half-maximum (FWHM) calculation result simultaneously. With this approach, it becomes possible to two-dimensionally visualize the relationship with fluctuation of the heart rate, thereby making it possible to give useful judgment materials in the diagnosis of a brain blood vessel system.

In the process of calculating the power ratio, by excluding in advance 1/f spectrum components of the power spectrum, it is possible to evaluate the nature of blood vessel more accurately. The 1/f spectrum component is of a spectrum structure which does not have any characteristic frequency that is often observable in the power spectrum of a living body, in particular, such as the blood pressure, heart rate, etc., and is considered to be the one that indicates that it is generated from a feedback structure with complicated blood-pressure/heart-rate changes, although details of its generation mechanism remains unknown yet.

Figure 7:
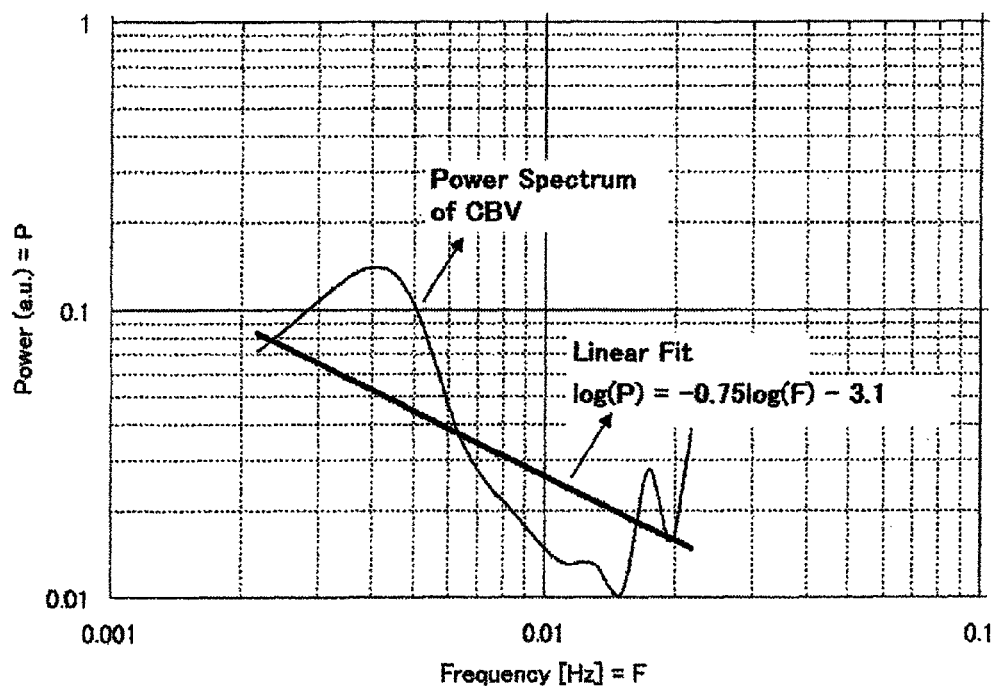
FIG. 7 shows an example of least-square fitting to $1/f^\alpha$ line in a double-logarithmic chart of CBV power spectrum.

A method for excluding in advance the 1/f spectrum component is as follows. Firstly, the power spectrum is plotted in a double logarithmic display, followed by letting a low-frequency portion be approximated by a straight line:
[Equation 2] (see FIG. 24),
where the gradient α denotes a power index of 1/f spectrum component. The least-square method is used to determine α and β of these parameters, thereby calculating the spectrum with a linear portion(s) being removed therefrom. When performing the calculation using the least-square method, an attempt is made to prevent data of the above-noted LF and VLF regions from being included therein. See FIG. 7, which shows a double logarithmic plot of the power spectrum of regional cerebral blood volume variation at the low-frequency component (e.g., 0.0022-0.022[Hz]), which plot was approximated by a line segment using Equation 1.

Embodiment 2

Figure 8:
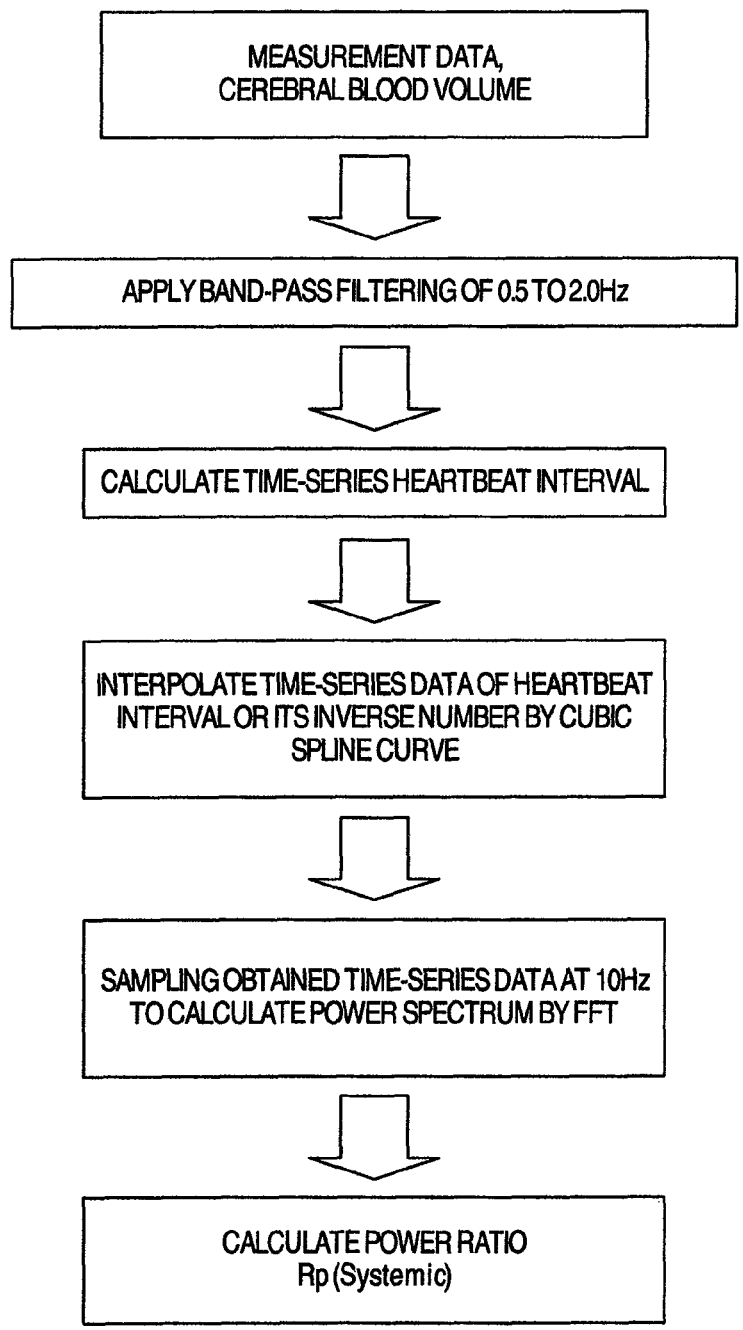
FIG. 8 is a flow for obtaining a heart rate variation.

$R_P$ (CBV) As an alternative to using the power ratio that was directly obtained from the regional cerebral blood volume variation in the embodiment 1, analysis is performed by $R_P$(pCBV) obtainable from the heart rate variation along a flow of FIG. 8. Here, the symbol pCBV represents pulsatile components of CBV. What is done first is to obtain a heart rate variation from the regional cerebral blood volume variation. An exemplary approach to obtaining the heart rate variation is to plot, in a time-series manner, the inverse number of a pulsating time period (nearly equal to R-R interval) which is obtainable from the data after having multiplied a band-pass filer frequency (0.5-2.0 Hz) to the regional cerebral blood volume variation. An uprising point of the extracted heartbeat component corresponds to a time point of R wave of electrocardiogram. In this example a pulsation interval was calculated by letting the time point of a minimal point that is between peaks of the extracted heartbeat components be an R-wave time point. Although this correspondence is reasonable in a physiological sense, no problems occur in the following discussion of the power spectrum even when letting each peak time point be the R-wave time point. The heart rate at each time point is imputed or "relegated" to its following heartbeat point (e.g., a time point having the minimum value in a heartbeat fundamental wave). The time-series heart rate variation obtained in this way is such that data point is identical to heartbeat point in the absence of a fixed length of period; so, this is subjected to interpolation using an appropriate method, such as a cubic spline curve, to thereby reshape the heart rate variation data. The resultant time-series data of heart rate variation is applied sampling at an appropriate sampling frequency (e.g., 10 Hz), thereby obtaining the power spectrum by fast Fourier transformation (FFT).

$R_P$ Regarding this power spectrum, VLF and LF components are used to calculate the power ratio in a similar way to the embodiment 1. Note that in the process of this power ratio calculation, excluding in advance 1/f spectrum components of the power spectrum makes it possible to evaluate the nature of blood vessels more accurately. The method of removing such 1/f spectrum components is the same as that stated in the embodiment 1.

$R_P$ The one that is obtained from the heart rate variation obtainable by execution of the processing of the regional cerebral blood volume variation in this way is closer to the systemicity than the power ratio $R_P$ (CBV) that was obtained directly from the regional cerebral blood volume variation; thus, let it be given by $R_P$ (Systemic). More precisely, $R_P$ (Systemic) is represented by:
[Equation 3] (See FIG. 24).

Figure 10:
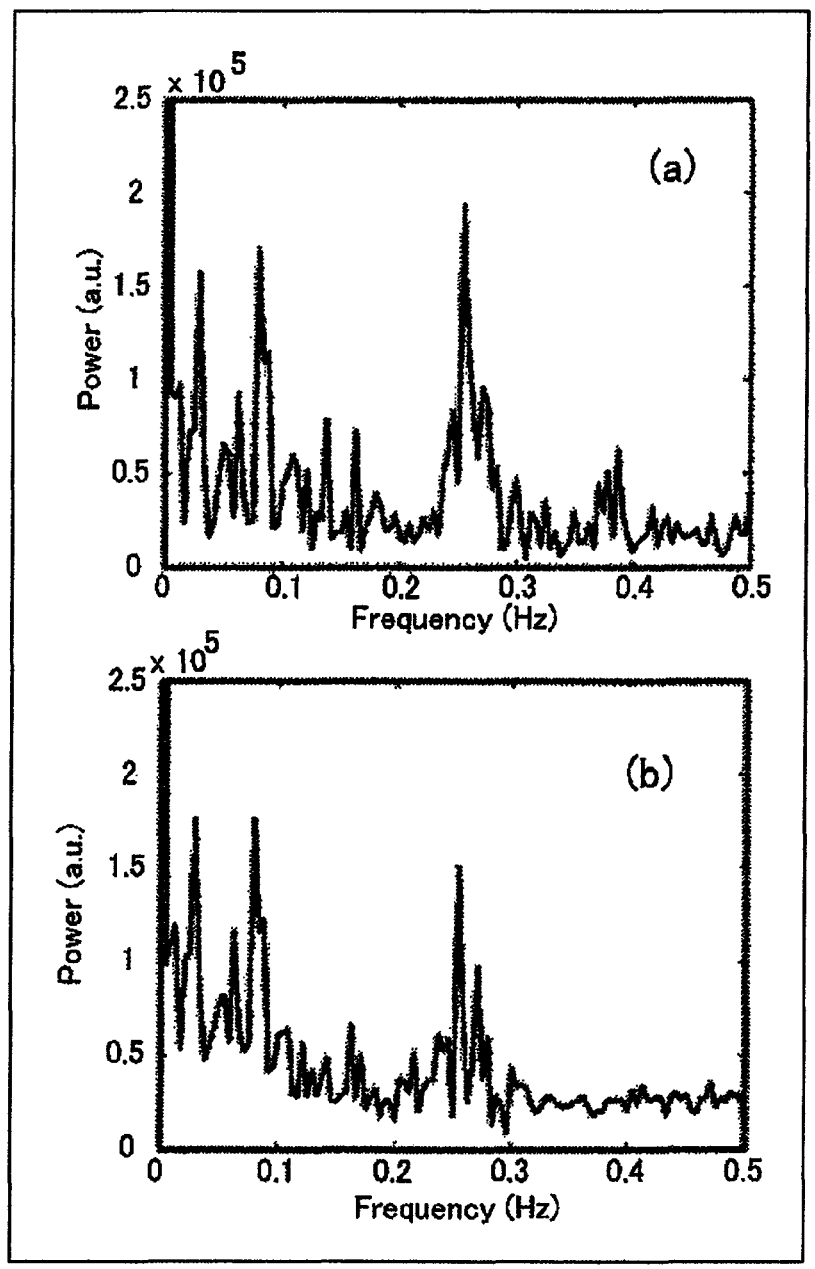
FIG. 10 shows power spectra of CBV and pCBV.

$R_P$ (Systemic) The validity of the analysis above was affirmed by experimentation. Regional cerebral blood volume (CBV) measurement at a forehead and electrocardiographic measurement were performed in an external trigger synchronized way. One exemplary result is shown in FIG. 10. Parts (a) and (b) show power spectra of the heart rate of pulsatile component of CBV (pCBV) measured at one point of the forehead and electrocardiogram heart rate (HR) within a frequency zone of 0-0.5 Hz. It can be seen that these power spectra are very similar to each other. In Table 1 below, respective $R_P$ values are compared with respect to two age-different subjects being tested. Furthermore, values of the augmentation index (AI), which is a parameter of systemic arterial sclerosis, are indicated for comparison. The AI value is a mathematically reduced value to the case of a hear rate of 75: as this value becomes smaller, the blood vessel of interest is thought to be greater in softness. As apparent from Table 1, each subject is shown to have two kinds of $R_P$ values that are almost the same as each other, which suggests the capability of approximately using the $R_P$ value of CBV hear rate. Additionally, aging leads to a decrease in each $R_P$ value and an increase in AI value. This shows a tendency toward the hardening of a blood vessel(s).

TABLE 1

Comparing each $R_P$ value to AI value

| Age of Subject (years) | CBS Heart Rate $R_P$ (pCBV) | ECG Heart Rate $R_P$ (HR) | AI Value (%) |
|---|---|---|---|
| 27 | 1.58 | 1.66 | 45 |
| 50 | 1.03 | 1.10 | 69 |

Figure 9:
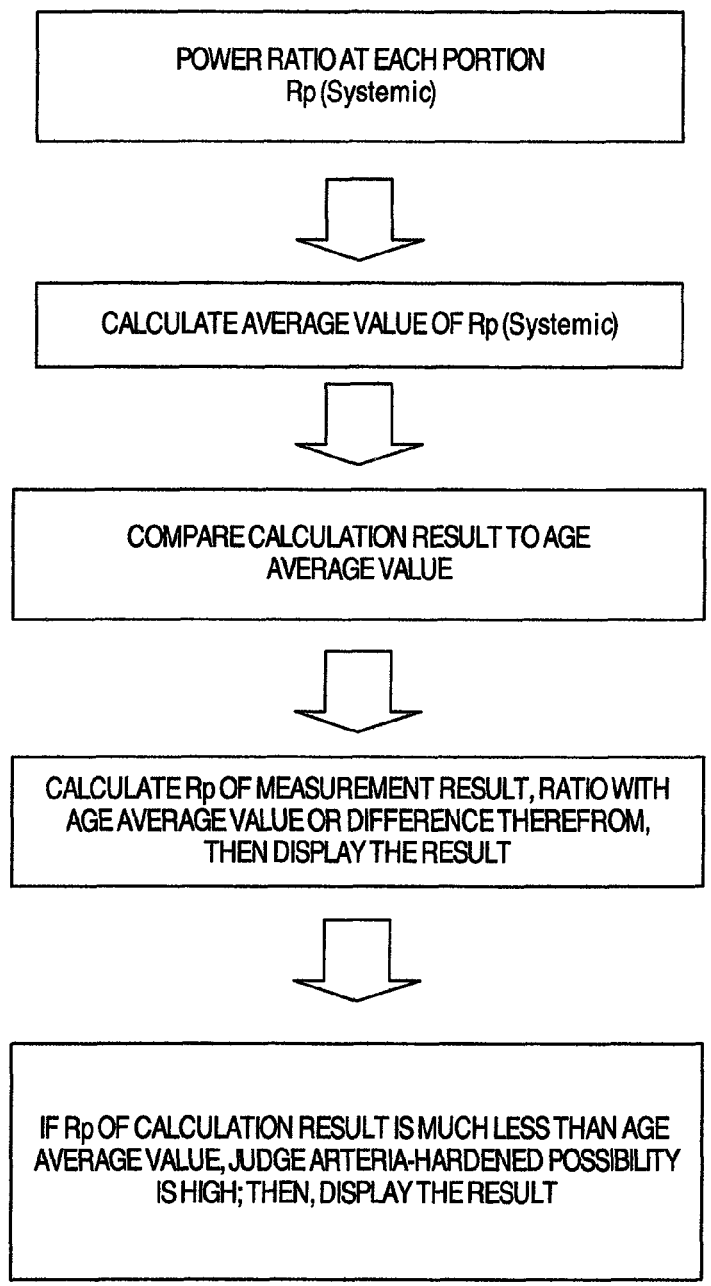
FIG. 9 is a flow for judgment of arterial sclerosis from only the average value of Rp (Systemic) at respective measured portions.
Figure 11:
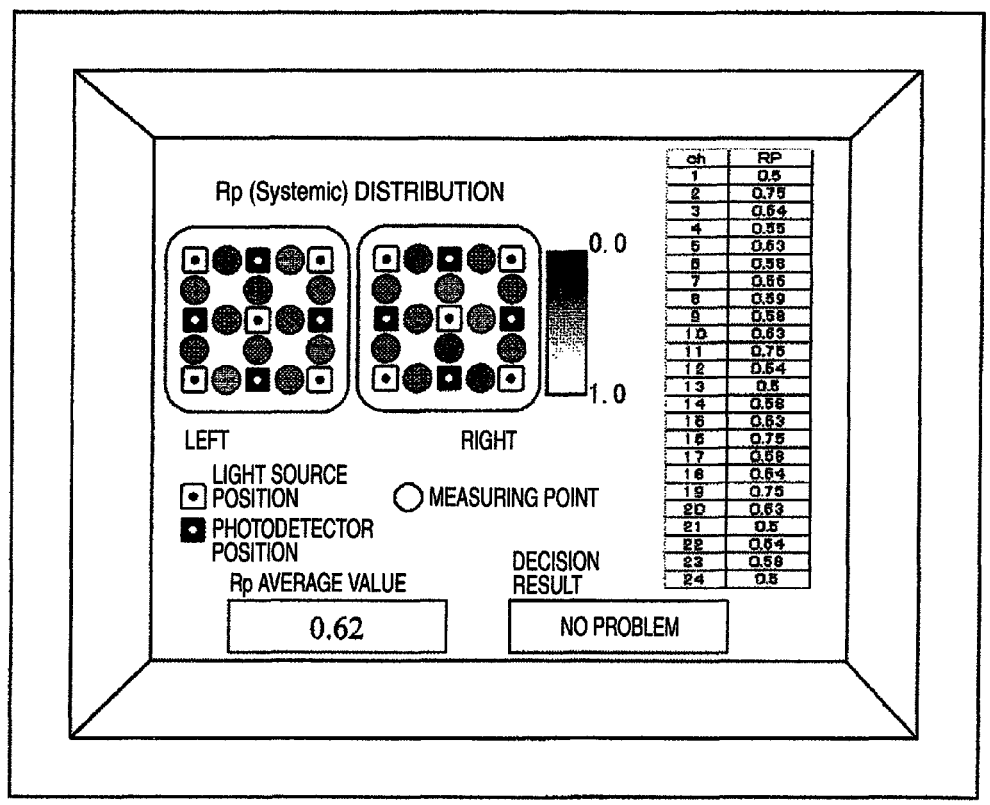
FIG. 11 shows a display of judgment result of arterial sclerosis degree from 2D distribution of Rp (Systemic) and the average value thereof.

$R_P$ (Systemic) is calculable at each portion of the head being tested. It is also possible to perform the mapping of $R_P$ (Systemic) of each portion. Here, there will be described an example using $R_P$ (Systemic) as averaged between respective measurement points. As previously stated, $R_P$ (Systemic) is the one that becomes a smaller value by the aging and also by microangiosis as taught from M. L. Schroeter et al., Journal of Cerebral Blood Flow & Metabolism, Vol. 24, pp. 1183-1191 (2004) and M. L. Schroeter et al., Journal of Cerebral Blood Flow & Metabolism, Vol. 25, pp. 1675-1684 (2005) and others. The age average value becomes smaller with an increase in age. $R_P$ (Systemic) that is less than the age average value suggests that the possibility of microangiosis or the degree of arterial sclerosis is high. Hence, by comparing $R_P$ (Systemic) to the age average value, the entire body's arteria is diagnosed to be hard when it is less than the age average value. It is also possible to use the magnitude correlation with the age average value or the ratio relating thereto as the criterion for evaluation. A process flow of the diagnosis becomes a flow such as shown in FIG. 9. More specifically, as shown in FIG. 11, $R_P$ of each measured portion is mapped; then, a calculation result of its average value is displayed along with a judgment result of the arterial sclerosis degree. In FIG. 11, the significance of $R_P$ is indicated by a gradation of black and white on a 2D map whereas $R_P$ values of respective channels are displayed in the form of a table. These $R_P$ values of respective channels may alternatively be displayed on the map. Regarding a distribution of $R_P$, only either one of the 2D map and table may be displayed. With such arrangement, it becomes possible to assist the diagnosis of heart disease or the like due to the hardness of systemic arteria.

When [Formula 4] (see FIG. 24) is satisfied, the arterial sclerosis is readily occurrable systemically; thus, the cerebral vascular disturbance also tends to easily take place. A threshold value TH1 was set to 0.1. This value was determined based on preliminary investigation with a medically sufficient number of subjects being as target bodies for inspection. With the use of this reference, the two subjects listed in Table 1 show a sufficiently large value as the $R_P$ value; so, it cannot be said that the cerebral vascular disturbance readily takes place.

$R_P$ (CBV) Similarly, when [Formula 5] (see FIG. 24) is satisfied with respect to the power ratio which is obtained from the power spectrum of the CBV per se as obtained in the embodiment 1, it is considered that there is the tendency that arterial sclerosis is easily occurrable and, therefore, the cerebral vascular disturbance also tends to readily take place. Additionally, the threshold value TH1 is set at 0.1.

In this embodiment, a fixed band-pass filter was used for simplification when extracting a pulsate component(s) appearing in CBV. In order to perform the extraction accurately, the processing may be done in a way which follows. Firstly, a power spectrum is obtained from the CBV's variation data. Then, let a frequency of the strongest peak within the range of 0.5-2.0 Hz be the fundamental frequency $f_0$ of heartbeat. Next, band-pass filter of a pass-through region $[f_0-0.5\ Hz, f_0+0.5\ Hz]$ is applied thereto, thereby obtaining a pulsate component pCBV. By use of this method, it becomes possible to extract the heartbeat component(s) more accurately.

Also note that the value of the index $\alpha$ in the $1/f$ spectrum component that was calculated in the process of this calculation also includes the information as to the blood vessel hardness. This is thought to be caused by the fact which follows: in cases where the complicated feedback mechanism is partially destroyed by the aging of a live body, it comes to have more random nature. In reality, according to the teachings of Castiglioni, P.; Frattola, A.; Parati, G.; Di Rienzo, M.; Engineering in Medicine and Biology Society, 1992, Vol. 14, Proceedings of the Annual International Conference of the IEEE Volume 2, Issue, 29 October-1 November, pp. 465-466 (1992) and Ichimaru Y, Ogasawara M, Katayama S, BME, 8 (10), pp. 36-48 (1994), the $1/f$ fluctuation phenomenon in low-frequency band is related to the aging and/or illness. The Castiglioni, P.; Frattola, A.; Parati, G.; Di Rienzo, M.; Engineering in Medicine and Biology Society, 1992, Vol. 14, Proceedings of the Annual International Conference of the IEEE Volume 2, Issue, 29 October-1 November, pp. 465-466 (1992) suggests that the $1/f$ spectrum appearing in arteria blood-pressure variation is analyzed for subject groups of young people and old people to reveal the fact that subjects of old people is appreciably large in value of the index $\alpha$.

Figure 12:
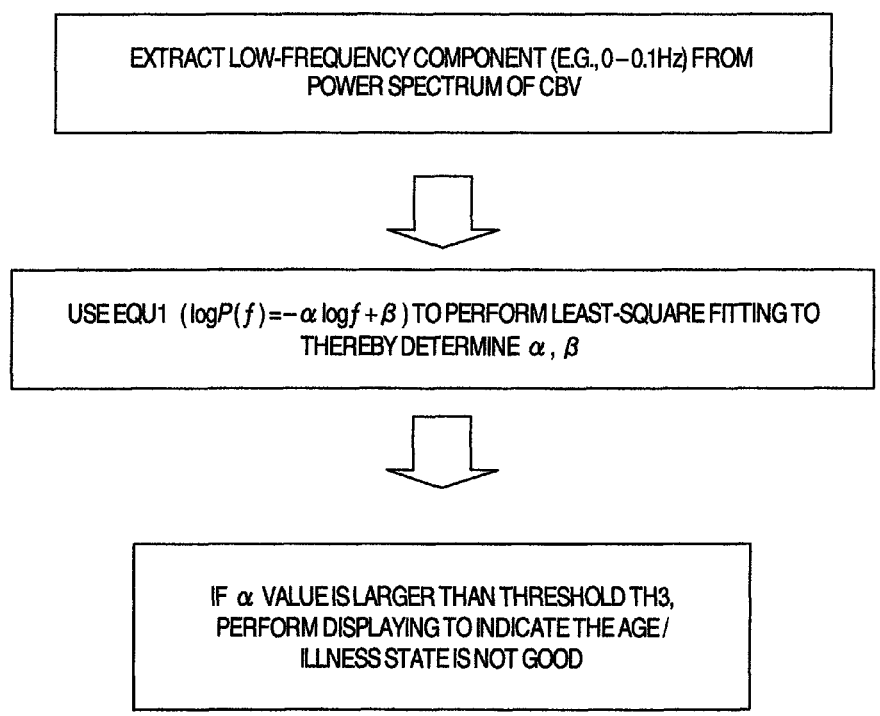
FIG. 12 shows a flow for judgment of aging and pathological state by means of $\alpha$ of $1/f^\alpha$.
Figure 13:
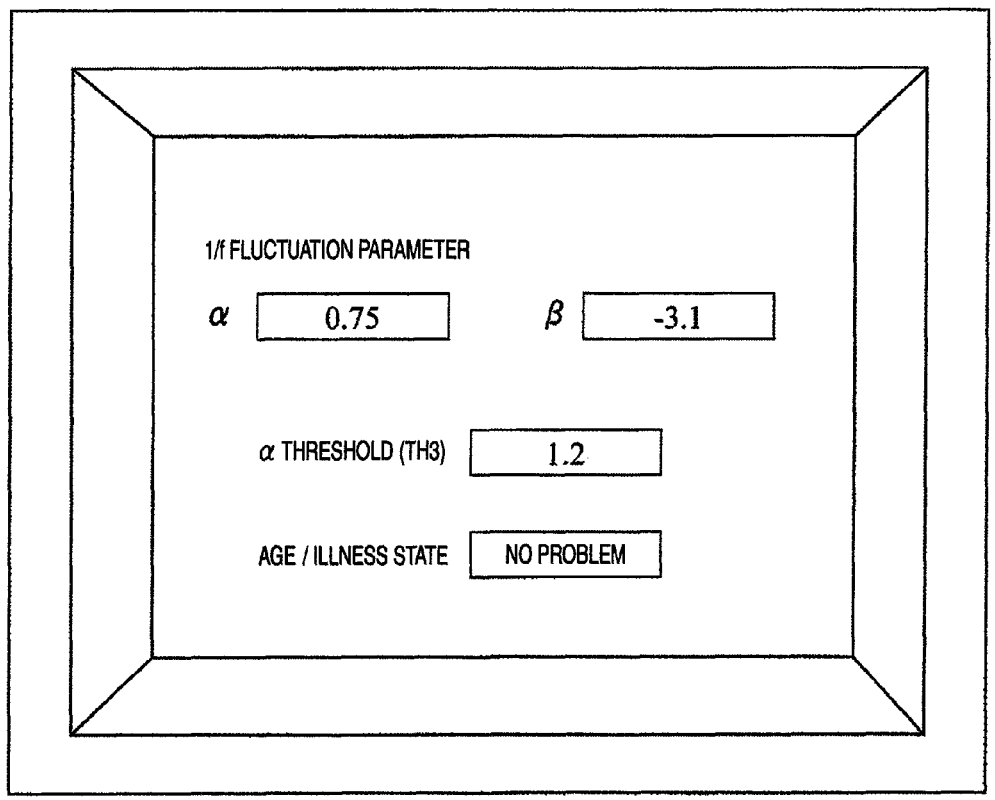
FIG. 13 shows a display example of judgment result of aging and pathologic state from 1/f fluctuation.

$R_P$ (CBV) This information alone, or in combination with the information of half bandwidth of heartbeat component, is utilizable for the judgment of a brain blood-vessel state. A process flow of the processing is shown in FIG. 12. First, a low-frequency component (e.g., 0-0.02[Hz]) is extracted from the power spectrum of CBV. Next, [Equation 2] is used to perform least-square fitting to thereby determine $\alpha$ and $\beta$. Lastly, when the value of $\alpha$ is greater than a threshold value (TH3), displaying is performed to indicate that the aging/illness state is not good in a manner shown in FIG. 13. Note here that TH3 is dependent on the age and life environments and usually falls within a range of from about 0.5 to about 2.0 (this is settable to 1.2, for example, by taking account of the data of the Castiglioni, P.; Frattola, A.; Parati, G.; Di Rienzo, M.; Engineering in Medicine and Biology Society, 1992, Vol. 14, Proceedings of the Annual International Conference of the IEEE Volume 2, Issue, 29 October-1 November, pp. 465-466 (1992)). Although it is desirable that the frequency range of the power spectrum to be used when obtaining a is set to about 0.02[Hz] or below, an entirety of the frequency range with the power spectrum being used therein may also be employed.

If the generation mechanism of $1/f$ fluctuation components is clarified more successfully in near feature, it is expected that the result of a or else is usable for the assistance of more practical diagnosis.

Embodiment 3

By using both the power ratio $R_P$ (CBV) that was directly obtained from a regional cerebral blood volume variation in the embodiment 1 and the $R_P$ (Systemic) (at each measurement point) which is obtainable from the heart rate variation that is obtained by processing of a regional cerebral blood volume variation as has been stated in the embodiment 2, calculation is performed to define the large/small relationship (or ratio of the both) of $R_P$ (CBV) and $R_P$ (Systemic) at each measurement point of the head of a live body.

$R_P$ For example, when the cerebral blood vessel system is extremely smaller than the systemicity, i.e., if $R_P$ (CBV)<<$R_P$ (Systemic), this means that the cerebral blood vessel system's arterial sclerosis degree is larger than the systemic arterial sclerosis degree; thus, it is judged that special care should be taken to prevent the cerebral vascular disturbance, such as stroke or else.

If the both are almost equal to each other, i.e., when $R_P$ (CBV)≈$R_P$ (Systemic), the systemic arterial sclerosis degree is judged by comparison with the average age value as in the judgment of the embodiment 2.

$R_P$ If the systemicity is extremely less than the brain blood vessel system, i.e., when $R_P$ (CBV)>>$R_P$ (Systemic), it is judged that the subject of interest is believed to be free from the risk of cerebral vascular disturbance, such as stroke or else.

Figure 14:
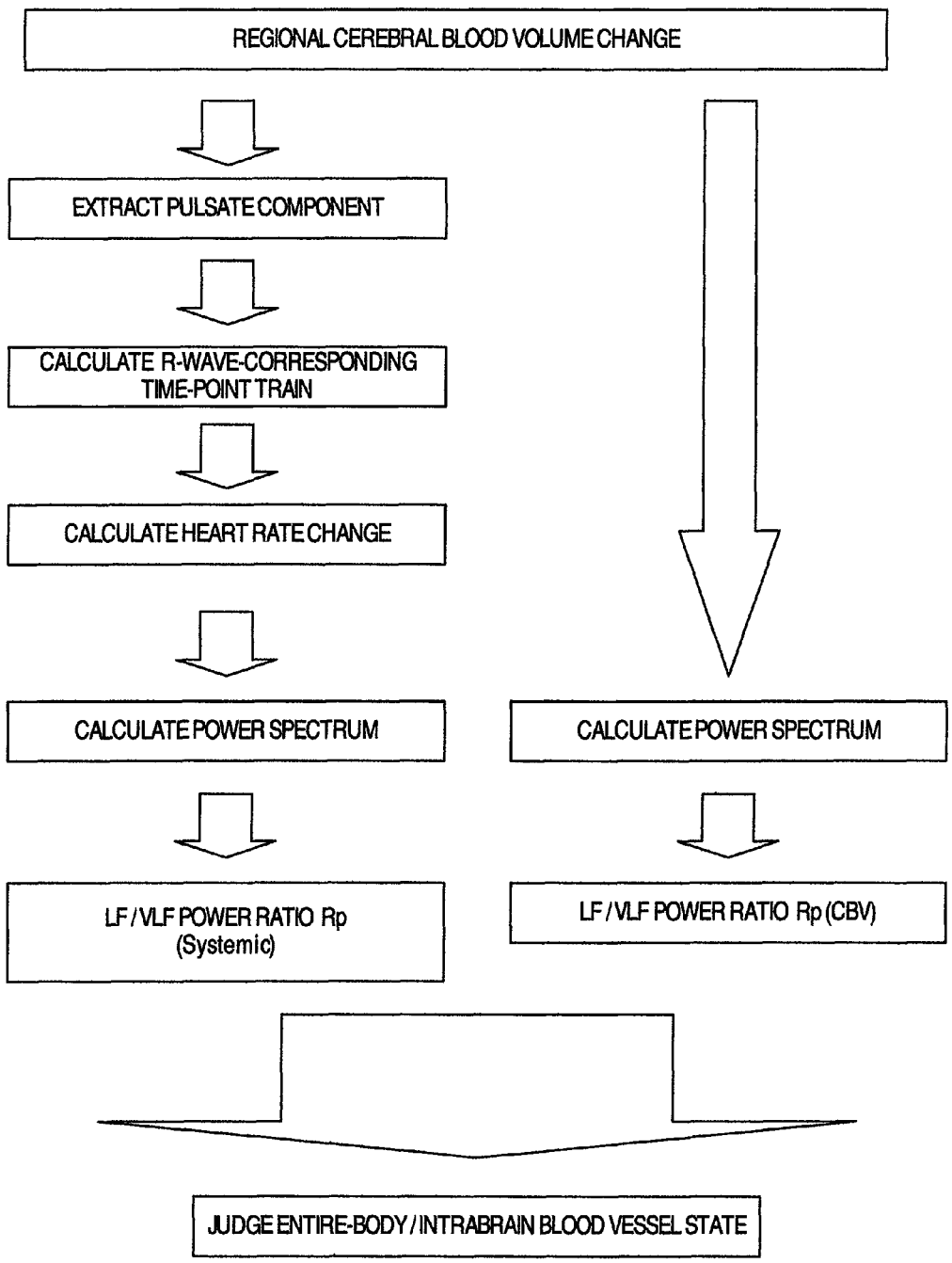
FIG. 14 shows a flow up to judgment of entire body and cerebral blood vessel state from regional cerebral blood volume variation only.

In this way, only the regional cerebral blood volume variation is used to estimate both the arterial sclerosis state of the systemicity and that of the cerebral blood vessel system whereby it becomes possible by using the both to perform diagnosis of cerebral vascular disturbance occurring due to arterial sclerosis, such as stroke or else. A flow of the processing is shown in FIG. 14.

$R_P$ (Systemic) The left-side part of this flow is similar to that in the case of the embodiment 2 whereas the right-side part is similar to that of the embodiment 1. At a decision step, the judgment relating to Formulas 4 and 5 is first performed independently. As a result, in case the Formulas 4-5 are satisfied, decision is further made to specify whether [Formula 6] (see FIG. 24) is met or not. In case Formula 6 is met, it can be seen that it is in the state that the cerebral vascular disturbance is extremely readily occurrable. Precise health examination is required. Note here that a threshold value TH2 is set to 0.2 under an assumption that this criterion is satisfied when it is more than five times greater than $R_P$ (CBV). This value also was determined based on preliminary investigation with a relatively less number of subjects being as target bodies. Additionally, in case the data of definitive diagnosis is stored as a database at a later stage, it is possible to improve it by automatic parameter adjustment functionality as will be described later.

Figure 5:
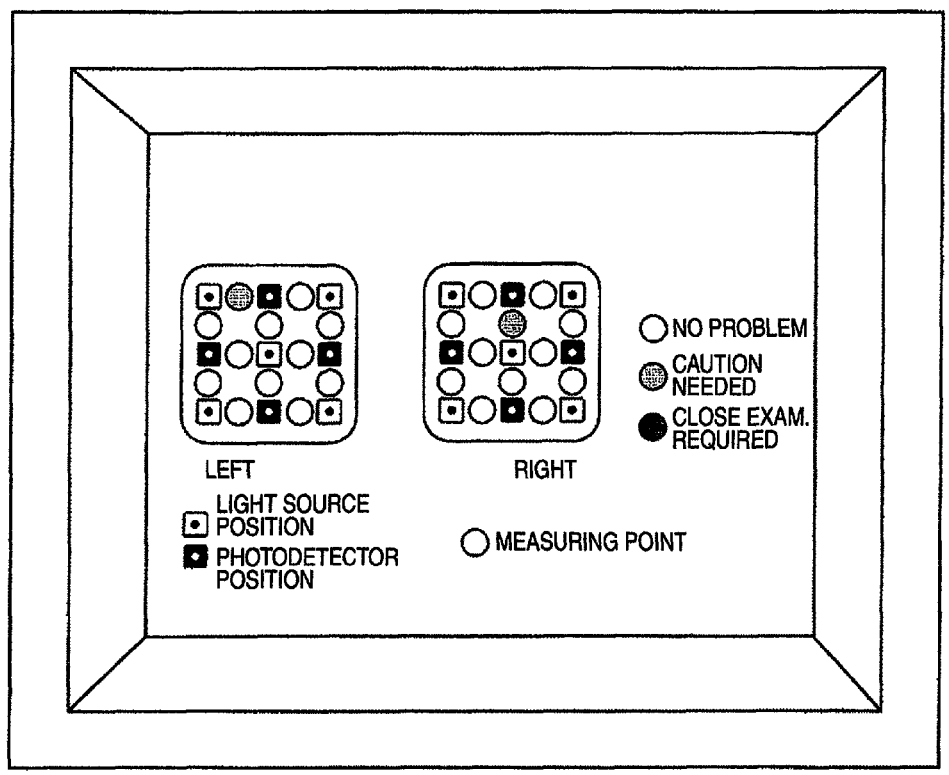
FIG. 5 shows an example of a result of two-dimensional (2D) mapping of $R_P$-based arterial sclerosis diagnosis results at a head part.

$R_P$ (CBV)<$R_P$ (Systemic) An example of the result with every right/left channel satisfying this formula is able to be displayed as shown in FIG. 5. Here, the degree of risk of the cerebral vascular disturbance is displayed in three ranks. The first phase: white: no problems. The second phase: gray: caution needed. The third phase: black: thorough checkup required. In this example, most part is in the first phase, and there were only two channels with the second phase being indicated thereat. In this way, visually displaying the cerebral vascular disturbance diagnosis result at the display unit makes it possible to give useful suggestions concerning a disease state to a doctor and/or a person inspected.

Figure 15:
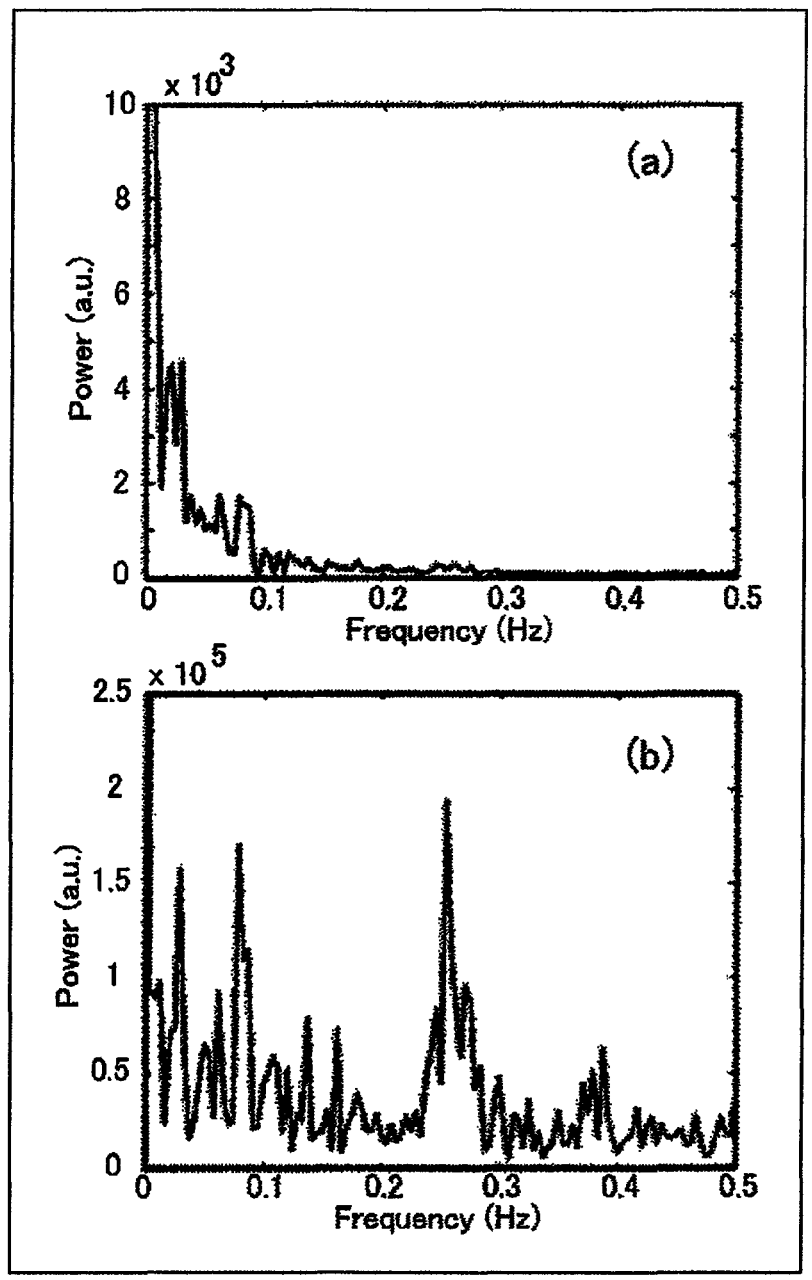
FIG. 15 shows power spectra of pCBV and heart rate.

$R_P$ (CBV) A measurement result of regional cerebral blood volume (CBV) at the forehead part is shown in FIG. 15. (a), (b) was measured at a one point of the forehead. It shows the power spectrum of low-frequency region of CBV, CBV heart rate (pCBV). The values of $R_P$ (Systemic) were 0.88 and 1.58, respectively. In Table 2 below, results of the same subjects as those in Table 1 are listed. The value of $R_P$ (CBV), $R_P$ (Systemic) decreases with an increase in age, which indicates the tendency of arterial sclerosis; however, it did not go beneath 0.5 for either one of the subjects. Thus it was made sure that it is hardly considered to be in the state that the arterial sclerosis was advanced within his or her brain.

TABLE 2

Comparing each $R_P$ value

| Age of Subject (yrs) | CBV $R_P$ (CBV) | Systemicity $R_P$ (Systemic) |
|---|---|---|
| 27 | 0.88 | 1.58 |
| 50 | 0.51 | 1.03 |

Figure 16:
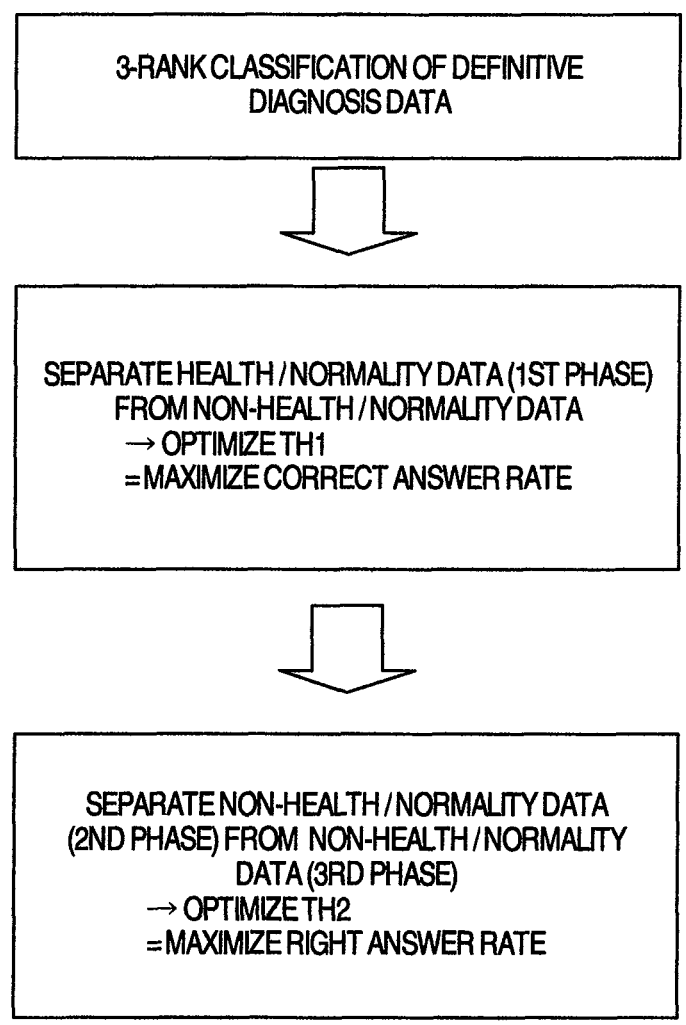
FIG. 16 shows a procedure of adjusting threshold value TH1, TH2.

The above-noted threshold values that were used in extraction of the information as to cerebral vascular disturbance are improvable by data accumulation. This apparatus has automatic adjustment function therefor. An adjustment procedure is summarized in FIG. 16. Firstly, respective channels of the data of execution of definitive diagnosis are classified into three categories which follow: "No problem," "Caution needed (progress is watched)" and "Thorough checkup required." Based on the information of the power ratio as stored in the storage unit, the threshold value TH1 is optimized. Although TH1 is the threshold for separation between the first phase and the others, TH1 is determined in a way such that the average of correct answer rates of respective groups becomes maximal in value. Next, the threshold value TH2 is optimized. TH2 is the threshold for separation between the second phase and the third phase. TH2 is determined so that it becomes the maximum of right answer rates with respect to respective groups. By combining with the definitive diagnosis information in this way, it is possible to modify or update them to more adequate threshold values.

Embodiment 4

Figure 17:
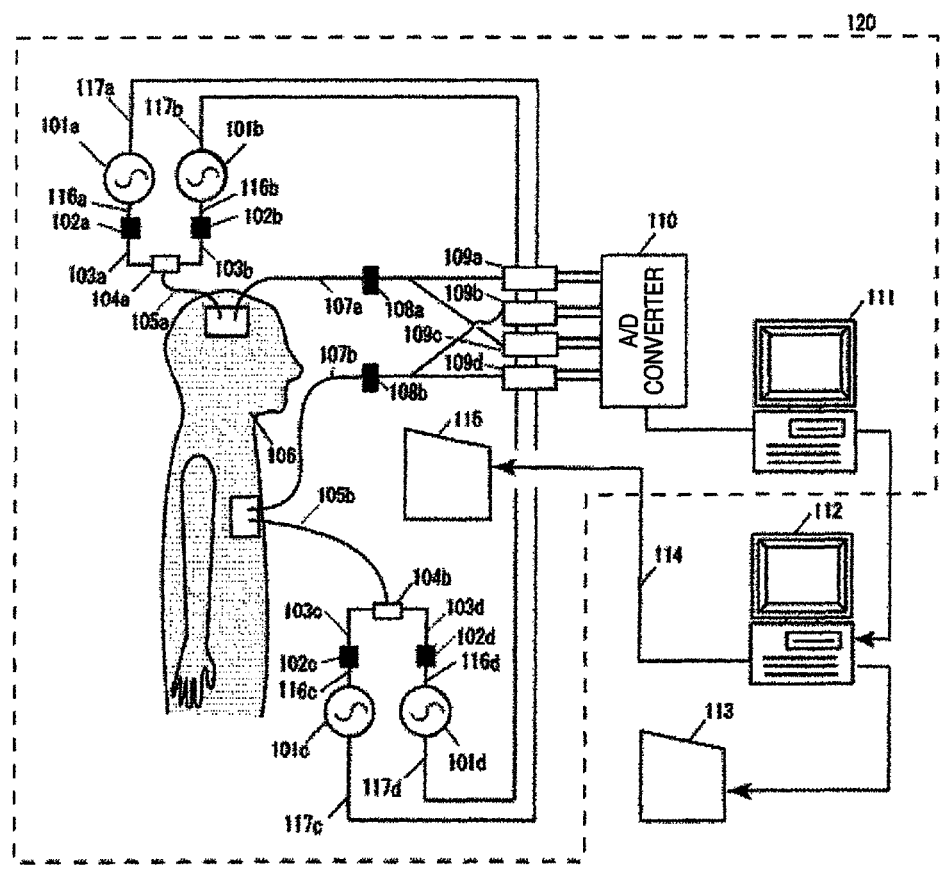
FIG. 17 is a configuration diagram in the event of simultaneous measurement of regional cerebral blood volume variations at a brain and a heart, spine or else.

In the embodiment 1, as shown in FIG. 17, a regional blood volume variation measurement unit which is constituted from part of the channel structure in the same system and which is placed at a location other than the head is used in addition to the measurement of the regional cerebral blood volume variation at the head to measure a regional blood volume change at a location other than the head of a body being tested (e.g., heart, spine, brachium, radial artery or fingertip). The both measurement portions are measured at a time. By this simultaneous measurement of multiple points using the same system, it is possible to measure phase differences and time differences at respective measured points without having to be affected by system-dependent time delays. A difference of FIG. 17 from FIG. 1 is that the optic fiber 103*b* and light-irradiating optic fiber 105*b* are situated at locations other than the head of the body being tested (e.g., heart, spine, brachium, radial artery or fingertip).

Figure 18:
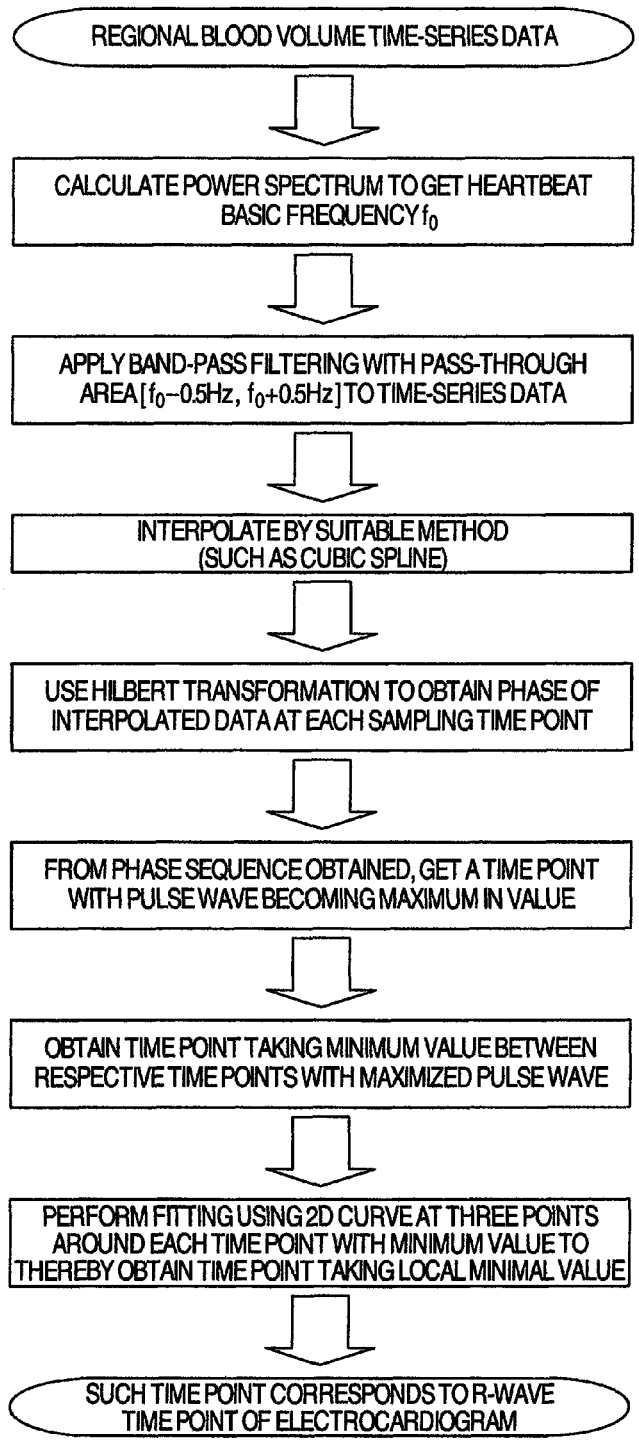
FIG. 18 shows a flow for calculation of a pulse wave time point string.

In order to obtain such phase differences and time differences of pulse waves at a plurality of portions, it is necessary to calculate the pulse wave's time point (instant corresponding to R-wave time of electrocardiogram) at each measurement point. A calculation flow of pulse-wave time-point sequence or "train" is shown in FIG. 18. First, the heartbeat's fundamental frequency $f_0$ is obtained from the power spectrum or the like of regional blood volume time-series data; then, band-pass filtering of the pass-through region [$f_0$−0.5 Hz, $f_0$+0.5 Hz] is applied thereto. For the resulting data, appropriate interpolation is performed, such as cubic spline or else. Next, Hilbert transformation is used to obtain the phase at each sampling time point of interpolated data. And, the phase sequence obtained is used to obtain a time point at which the pulse wave becomes at the maximum value; next, at a point midway between respective time points with the maximized pulse wave, a time point is obtained at which it takes the minimum value. At three separate points around each time point with such the minimum value being taken here, 2D curve-used fitting is performed, and let a time point whereat the minimum value is taken be the R-wave time point. Based on the R-wave time points thus obtained at respective measured portions, it becomes possible to calculate the phase differences and time differences between respective measured portions.

Figure 19:
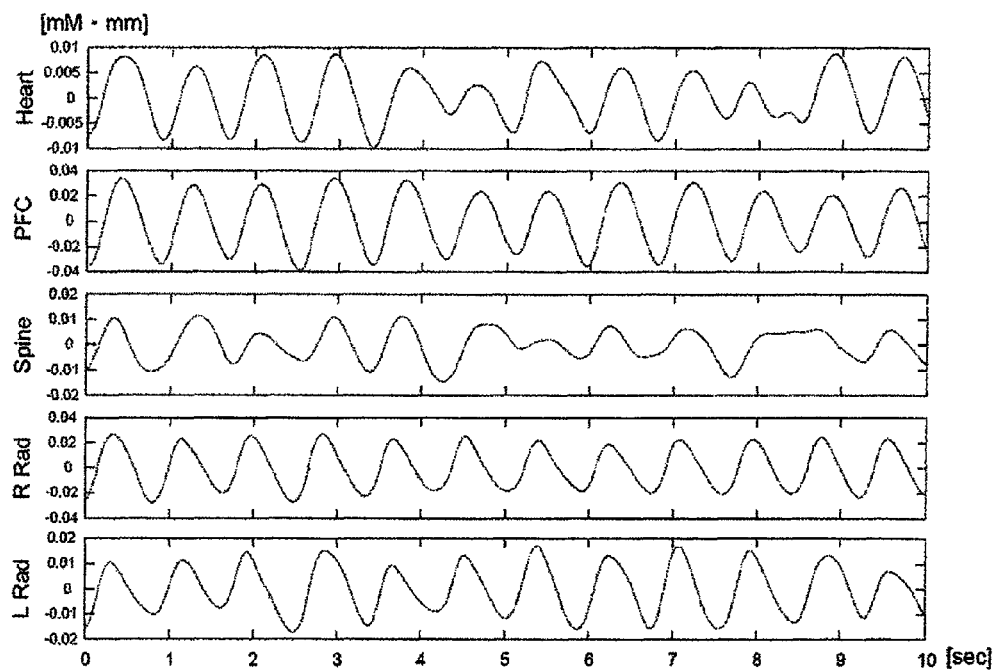
FIG. 19 shows measurement data (after interpolation using a band-pass filter) of oxygenated hemoglobin concentration changes when simultaneous measurement was done at five separate portions by use of a regional blood volume change measuring unit by means of probes which are set at a portion immediately above the heart, a head (prefrontal area), a portion above a spine (waist position), and portions just above radial artery (at right and left hands).

Oxygenated hemoglobin concentration change measurement data are shown in FIG. 19 in the case of simultaneous measurement of five portions by probes which are placed at a portion immediately overlying the heart, a portion on the head (prefrontal area), a portion on the spine (waist position) and portions just above radial artery (at right and left hands) with the actual use of the regional blood volume variation measurement unit (note that the "Heart" indicates the portion immediately above the heart; PFC is the prefrontal area; Spine, the portion just above the spine (waist position); R Rad, right-hand radial artery; L Rad, left-hand radial artery). It displays a change with time (10 seconds) of the oxygenated hemoglobin data. Each measurement portion is such that the unit of the vertical axis is [mMmm]. In this experimental data, when the method shown in FIG. 18 is used to obtain the pulse wave time point for each measurement portion to thereby obtain the average value of phase differences, pulse-wave time delays which are obtained from the measurement data of the prefrontal area, spine (lumbus), right-hand radial artery and left-hand radial artery) became 14.1 msec, 18.5 msec, −7.14 msec and −39.5 msec, respectively. In this way, it becomes possible to perform the analysis of measurement data of another measurement point with the pulse phase at a certain measurement portion (e.g., the heart) being as the reference of time axis.

In addition, continuous measurement of five minutes is performed while at the same time detecting respiration with eyes and entering a mark, whereby it was experimentally affirmed that these measurement data contain a breathing-synchronized component(s). By measuring the respiration simultaneously, it becomes also possible to perform the analysis of pulse wave more accurately while letting respiration components be excluded therefrom.

In this embodiment, the phase difference or time difference (transfer time) of a pulse wave which rides on the simultaneously measured regional cerebral blood volume variation (referred to hereinafter as intra-brain pulse wave) and a pulse wave riding on a regional blood volume variation at a location except the head (referred to as specific-region pulse wave hereafter) is used for the diagnosis of cerebral vascular disturbance, such as arterial sclerosis. Both the intra-brain pulse wave and the specific-region pulse wave have the same derivation that is the heartbeat so that their frequency changes must be almost the same as each other. Also note that the distance from the heart is kept substantially constant at any position of the head; accordingly, if it is assumed that the modus operandi of heartbeat transmission is the same, the spatial distribution of a phase difference between the specific-region pulse wave and the intrabrain pulse wave is expected to become continuous on a map. Hence, if the phase difference exhibits a discontinuous change on the map, this means that the modus operandi of heartbeat transmission within the brain is different depending on locations. Thus, it is considered that one of possible causes thereof lies in discontinuous distribution of the hardness state of arteria.

Figure 20:
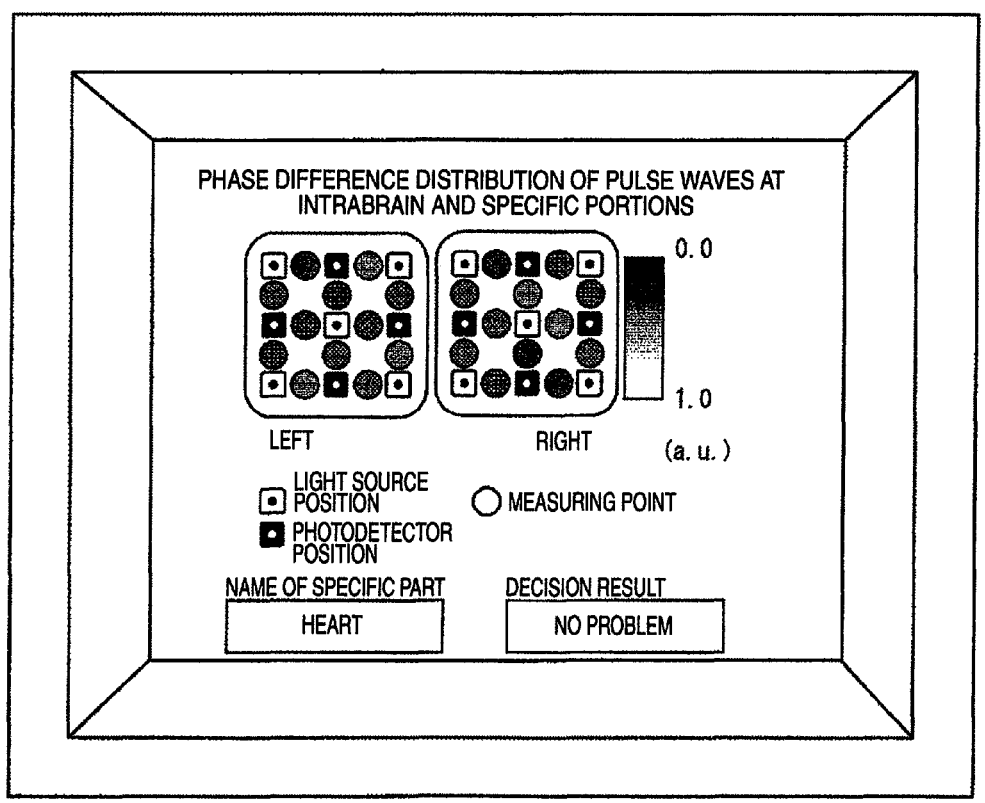
FIG. 20 shows a display example of a distribution of phase differences of cerebral pulse wave and specific-portion pulse wave.
Figure 21:
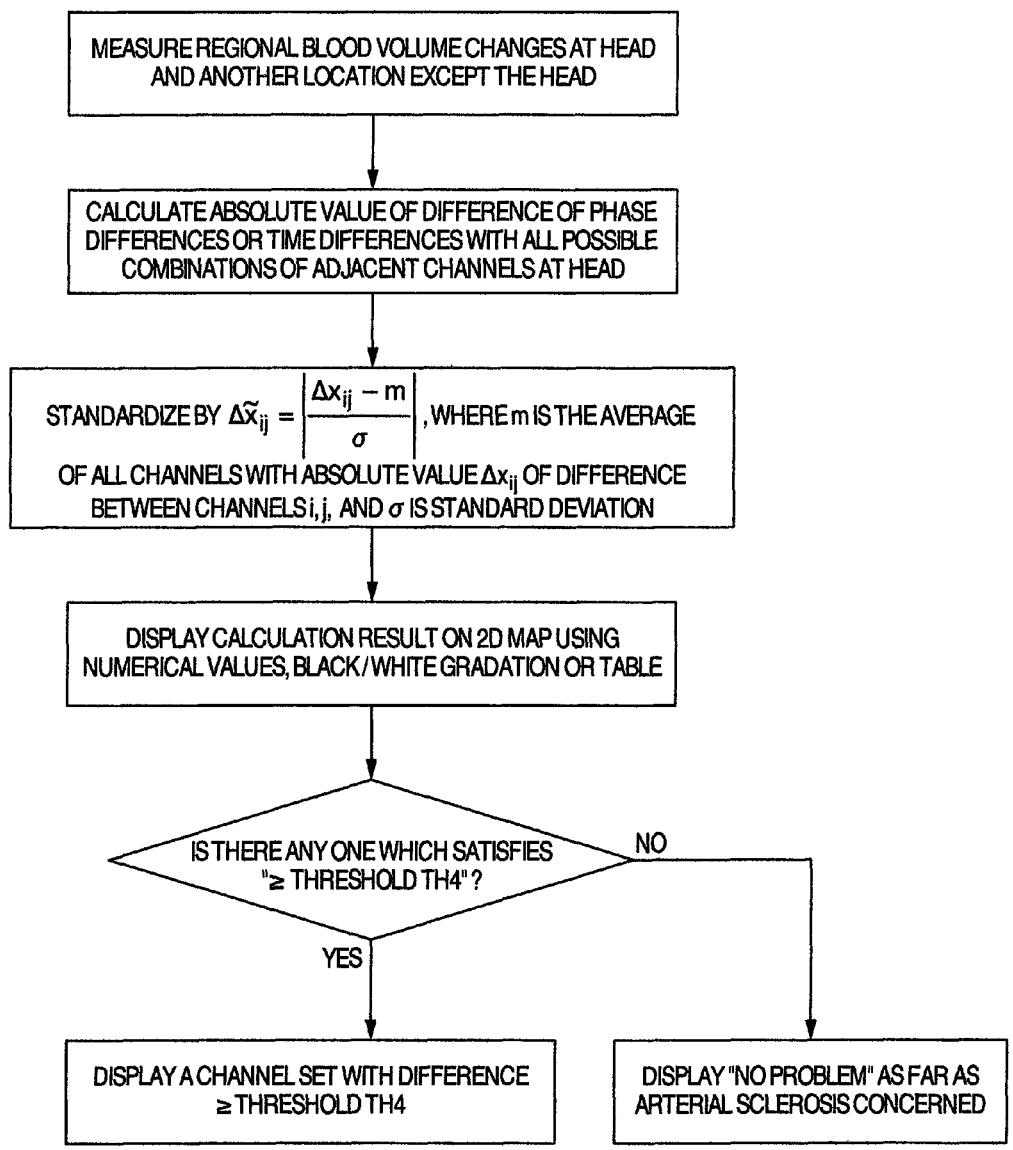
FIG. 21 shows a flow when assisting diagnosis of brain disease or the like by simultaneous measurement of regional blood volumes at a brain and a heart or spine or else.

In the actual diagnosis, a distribution (2D map) of the phase difference of the intrabrain pulse wave and specific-region pulse wave is displayed at the display unit, and if the difference exhibits a discontinuous change, then it is diagnosed that the possibility of arterial sclerosis is high, followed by displaying of a diagnosis result. A display example of the distribution of the phase difference and intrabrain pulse wave and specific-region pulse wave is shown in FIG. 20 along the result thereof whereas a flow of an entirety of this embodiment including the continuity judgment is shown in FIG. 21. More precisely, after having measured regional blood volume variations at the head and another location except the head, a difference of the phase differences or the time differences is calculated with respect to every possible combination between neighboring channels in the brain. Then, data standardization is performed for a calculation result, followed by displaying on 2D map in the form of numerical values or a black-and-white gradation pattern or a table. If the calculation result contains at least one with its value greater than or equal to a prespecified threshold value (TH4), its channel set is displayed numerically. If such is not found then "No problem" is displayed with regard to the arterial sclerosis.

For instance, TH4 is defined in a way which follows. Assuming that the distribution of standardized difference values is in compliance with the normal distribution, it is diagnosed that the possibility of arterial sclerosis is high when the probability generated takes a difference value of 5% or less. From the two-sided possibility of a normal distribution table, the probability of becoming a standardized difference value of 1.96 or more is 5%; so, it is possible to determine TH4=1.96.

In this way, if the standardized difference value is equal to or greater than TH4 then the possibility of arterial sclerosis is judged to be relatively high when compared to other locations. Otherwise, a decision is made to conclude there is no problem. This is a determination method which takes into consideration the fact that the average of phase differences of the intrabrain pulse wave and specific-region pulse wave varies between individuals. Regarding this threshold value determination method, it is an evaluation on the 2D map of the head, which concerns the relative occurrability of arterial sclerosis within the body of a one person under inspection; for comparison between individuals, a need is felt to use measurement values of many persons being tested and/or the average value of their ages. The threshold value TH4 determining method is not exclusively limited thereto, and other suitable methods may be used when the need arises.

In FIG. 20, an example is shown which indicates the phase differences by a black-and-white gradation pattern, although exact numeric values may also be laid out on this 2D map. By doing so, it is possible to perform diagnosis which takes into consideration such the 2D layout in addition to the information on the hardness degree of a blood vessel at each measurement point. Additionally, regarding the presence/absence of the continuity, there is also the effect of preventing oversight of a doctor or an operator of the apparatus, owing to the automated judgment by means of the computer.

As shown in this embodiment, in the apparatus for measuring regional blood volume variations, measurement portions are extended to a location(s) other than the head for simultaneous execution of measurement of the head and measurement at such location(s) whereby it becomes possible to measure phase differences of intrabrain pulse wave and specific-region pulse wave without having to use additional measurement system(s).

Note here that similar analysis is executable by using an electrocardiogram or a photoelectric volume pulse wave recorder (called the photo-plethysmography) or an invasive blood pressure meter or the like as an alternative to the regional blood volume variation measurement unit to be set at the location except the head, as used in this embodiment.

Embodiment 5

Figure 22:
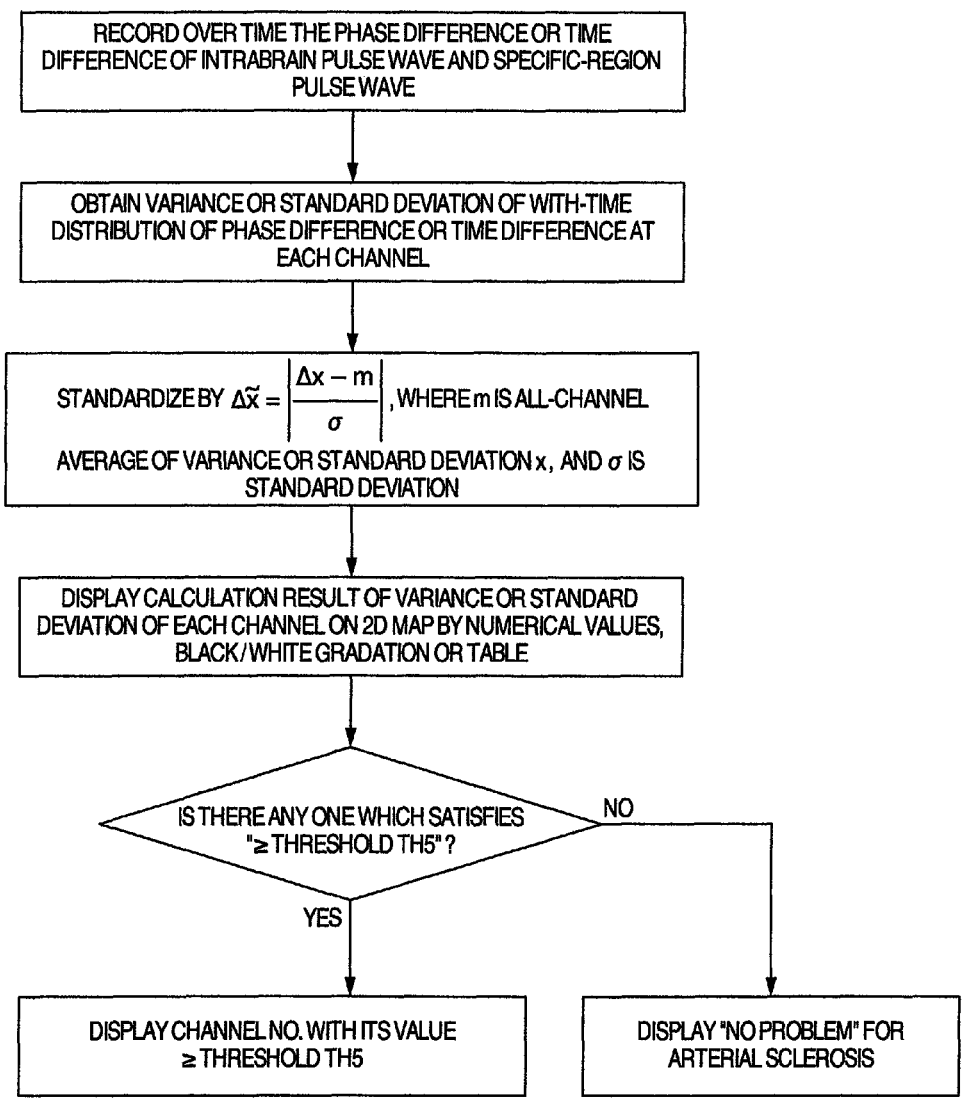
FIG. 22 shows a flow when assisting diagnosis of brain disease or the like while recording in a change-with-time manner a phase difference or time difference of cerebral pulse wave and specific-portion pulse wave.

In the embodiment 4, it is also possible to measure with-time changes by recording, over time without limiting to a certain time point, phase differences or time differences of the intrabrain pulse wave and specific-region pulse wave. By obtaining the phase differences of the intrabrain and specific-region pulse waves in the form of time-series data in this way, it is possible to measure the intended fluctuation in terms of time. A variance or standard deviation is calculated at appropriate time intervals. When the variance or standard deviation is less in value, it indicates the fluctuation with time is small. This involves information of the hardness degree and/or blocked state of blood vessels: when the variance or the standard deviation is less, i.e., the with-time fluctuation is small, it is very likely that the blood vessel of interest is hard and, therefore, the possibility of arterial sclerosis is high. Accordingly, by displaying, on a 2D map for example, the variance of phase differences of intrabrain pulse wave and specific-region pulse wave, it is possible to make a decision of caution needed for arterial sclerosis as the possibility of arterial sclerosis is high in regard to a measurement point with its value less than or equal to a preset threshold value and then display it on the monitor screen. The display of such result becomes the same as the one with the phase difference distribution of FIG. 20 being replaced by a distribution of the variance or standard deviation. As for the judgment of illness or else, a flow of processing is shown in FIG. 22. After having recorded with time the phase differences or time differences of the intrabrain pulse wave and specific-region pulse wave, the variance or standard deviation is obtained at each channel. Next, data standardization is performed with respect to the variance or standard deviation at each channel, followed by displaying of a result on 2D map by using numerical values or a black-and-white gradation pattern or in the form of a table. Among them, regarding the variance or standard deviation, an attempt is made to check whether there is the one with its value less than or equal to a certain threshold value (TH5, which is different depending on whether the variance or the standard deviation is used). The fact that the variance or standard deviation is small means that the pulse wave is less in fluctuation, which in turn denotes the possibility of arterial sclerosis is much higher. And, if there is a channel with its value less than or equal to the threshold TH5, then display its channel number; otherwise, a text is displayed, which indicates "No problem" as far as the arterial sclerosis is concerned.

TH5 is defined, for example, in a way which follows. Assuming that a distribution of the standardized measurement values (variance or standard deviation) follows the normal distribution, when the measured value is a value which is less than or equal to one-side possibility of 5% in the direction of smaller values, it is diagnosed that the possibility of arterial sclerosis is high. From the one-side possibility of the normal distribution table, the possibility of becoming a standardized measurement value of −1.645 or less is 5%: so, it is possible to determine TH5=−1.645.

In this way, if the data with standardization of the variance or standard deviation of phase differences or time differences is less than or equal to TH5 (different depending on whether the variance or standard deviation is used) then judge that the possibility of arterial sclerosis is relatively high when compared to other locations. Otherwise, it is judged that there are no problems. This is a determination method which takes into consideration the fact that the average of with-time distribution of phase differences of the intrabrain pulse wave and specific-region pulse wave can vary between individuals. Concerning this threshold value determination method, it is an evaluation on the 2D map of the head, which concerns the relative occurrability of arterial sclerosis within the body of a one person under inspection; for comparison between individuals, it is needed to use measurement values of many persons being tested and/or the average value of their ages. The threshold value TH5 determining method is not exclusively limited thereto, and other suitable methods may be used when the need arises.

Additionally, by co-use of the judgment shown in the embodiment 4, it is possible to enhance the certainty of the diagnosis of cerebral vascular disturbance.

In a similar way to the embodiment 4, it is also possible to perform similar analysis by using an electrocardiogram or a photoelectric volume pulse wave recorder (called the photoplethysmography) or an invasive blood pressure meter or the like in place of the regional blood volume variation measurement unit to be set at the location except the head, as used in this embodiment.

Embodiment 6

Figure 23:
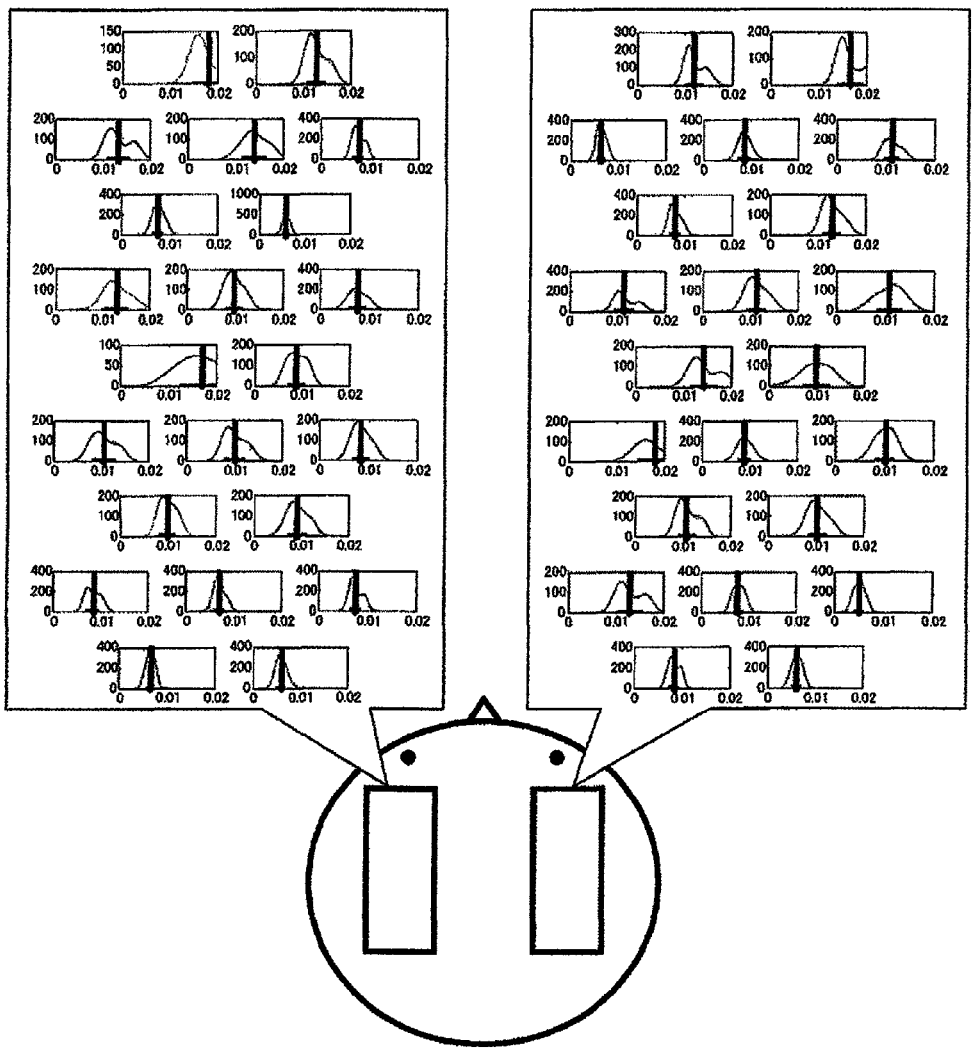
FIG. 23 shows a display example of brain blood flow distribution as estimated from cerebral pulse wave shape.

In this embodiment, the regional cerebral blood volume variation distribution is estimated from the shape of a pulse wave component which exists within a band of from 1 Hz to 1.5 Hz of a regional cerebral blood volume variation that was separated by a simplified technique in the embodiment 2. Although a pulsatile component of cerebral blood flow (pCBF) is the physical quantity that is different from the pulsate component of cerebral blood volume (pCBV), the pCBF may be approximated to be the temporal differentiation of pCBV, i.e., the gradient thereof. Within the wavelength range of the light source as used in this embodiment, the pulse wave observed is different in shape from a large artery because of mainly looking at the information of capillary blood vessels (as taught, for example, from Rasmussen, P. et al., Journal of Cerebral Blood Flow & Metabolism, Vol. 27, pp. 1082-1093 (2007)). In pulsation, a change in blood vessel diameter is ignorable so that the above-stated approximation is through to be proper. As found in Themelis, G. et al., Journal of Biomedical Optics, Vol. 12, 014033 (2007), the maximum value of gradient values of respective beats of the pulse wave was regarded as its corresponding regional cerebral blood volume value. The gradient was computed in a way which follows. Spline interpolation is applied in such a manner that the sampling interval becomes 10 milliseconds at each measurement position (channel). The gradient was obtained through linear approximation of each point and its five precedent and five following points (11 points in total) at time intervals of 10 milliseconds. For each beat, a maximal value of the gradient was recorded at each channel. From the values recorded, a distribution density function of the regional cerebral blood volume was obtained by kernel estimation, for example. A distribution of cerebral blood volumes each of which was estimated from the intrabrain pulse wave shape is shown in FIG. 23. At lower part of this diagram, probe positions on the human head being tested are indicated by rectangles. The layout of graphs within a balloon is identical to the layout of channels within its corresponding one of the rectangle-depicted probe layout areas on the human brain. At each channel position, the distribution density function of regional blood volume is indicated. The abscissa axis represents the blood flow value whereas the vertical axis denotes the distribution density. The average value of regional blood flows is indicated by a thick vertical line, with the standard deviation being associatively displayed using a thick transverse line. In this example, a decrease in blood flow is observed in a posterior parietal lobe region; however, its symptom is minimal.

The present invention is adaptable for use in cerebral vascular disturbance examination apparatus.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A biological measurement apparatus comprising:
a measurement unit configured to acquire information corresponding to a cerebral blood volume variation of a test body, and to output a first signal indicating the cerebral blood volume variation corresponding to the information; and
an analysis unit configured to:
acquire a first power spectrum calculated from the first signal;
acquire a second signal indicating heart rate variation calculated from the heartbeat intervals in the first signal;
acquire a second power spectrum based on the second signal;
calculate, from the first power spectrum, a first power intensity ratio which is a ratio of a power intensity in a predetermined first frequency band and a power intensity in a second frequency band; and
calculate, from the second power spectrum, a second power intensity ratio which is a ratio of the power intensity in the first frequency band and the power intensity in the second frequency band,
wherein the biological measurement apparatus is configured to output information regarding a brain blood-vessel state in accordance with a large/small relationship of the first power intensity ratio and the second power intensity ratio.

2. The biological measurement apparatus according to claim 1, wherein the information regarding the brain blood-vessel state is classified for each predetermined reference value which is preset and held, in accordance with the first power intensity ratio and the second power intensity ratio.

3. The biological measurement apparatus according to claim 1, wherein the biological measurement apparatus is configured to extract the information regarding the brain blood-vessel state by a relative relationship between the second power intensity ratio and preregistered reference data.

4. The biological measurement apparatus according to claim 3, wherein the relative relationship is at least one of a difference or a ratio between the second power intensity ratio and the reference data.

5. The biological measurement apparatus according to claim 1, wherein the first power intensity ratio and the second power intensity ratio are respectively acquired as a ratio of an average of a power spectrum density in the first frequency band and an average of a power spectrum density in the second frequency band.

6. The biological measurement apparatus according to claim 1, wherein the first and second power intensity ratios are calculated by performing processing for excluding 1/f spectrum components of the respective first and second power spectrums.

7. The biological measurement apparatus according to claim 1, further comprising a display unit configured to display a calculation result;
wherein the analysis unit is configured to control the display unit to display the information regarding the brain blood-vessel state.

8. The biological measurement apparatus according to claim 7, wherein the measurement unit has a plurality of light sources and a plurality of photodetectors configured to measure a plurality of measurement points; and
the display unit is configured for control to display the information regarding the brain blood-vessel state for each channel of the plurality of measurement points of a head.

9. The biological measurement apparatus according to claim 1, wherein the measurement unit has at least one of a light source configured to irradiate a light ray to a head of a test body and a photodetector configured to detect a light ray from the light source that has passed through inside of the test body.

10. The biological measurement apparatus according to claim 1, further comprising a storage unit configured to store at least one of a measurement result measured in the measurement unit, the specific region blood volume measurement unit, or a calculation result in the analysis unit; and
wherein the analysis unit is configured to refer to information stored in the storage unit and to extract information from the storage unit regarding the brain blood-vessel state for each measurement point of the test body.

11. The biological measurement apparatus according to claim 1, wherein the time series of heart rate signal is calculated from a pulsating time period.

12. A biological measurement apparatus comprising:
a measurement unit configured to acquire information corresponding to a cerebral blood volume variation of a test body and to output a signal indicating the cerebral blood volume variation;
a specific region blood volume measurement unit configured to measure information corresponding to a blood volume change at locations other than a head of the test body and to output a signal indicating a blood volume change at locations other than a head of the test body; and
an analysis unit configured to:
acquire a signal based on a pulse wave of cerebral blood;
analyze the blood volume change at locations other than the head of the test body and acquire a signal based on a pulse wave at locations other than a brain; and
analyze and output a phase difference or a time difference between the signal based on the pulse wave of the cerebral blood and the signal based on the pulse wave at locations other than the brain.

13. The biological measurement apparatus according to claim 12, wherein the measurement unit has at least one of a light source configured to irradiate a light ray to a head of a test body and a photodetector configured to detect a light ray from the light source that has passed through inside of the test body.

14. The biological measurement apparatus according to claim 12, further comprising a display unit configured for control to display a calculation result; and a distribution map of the phase difference or time difference between the pulse wave of the cerebral blood and the pulse wave at locations other than the brain.

15. The biological measurement apparatus according to claim 14, wherein the analysis unit is configured to control the display unit to display that a possibility of arterial sclerosis is high if there is a discontinuous change in a waveform of the phrase difference or the time difference.

16. The biological measurement apparatus according to claim 12, further comprising a storage unit configured to store at least one of a measurement result measured in the measurement unit, the specific region blood volume measurement unit, or a calculation result in the analysis unit; and
wherein the analysis unit is configured to refer to information stored in the storage unit and to extract information from the storage unit regarding the brain blood-vessel state for each measurement point of the test body.

17. The biological measurement apparatus according to claim 12, wherein the time series of heart rate signal is calculated from a pulsating time period.

* * * * *